US009593370B2

(12) United States Patent
Jones

(10) Patent No.: US 9,593,370 B2
(45) Date of Patent: Mar. 14, 2017

(54) BIOCHEMICAL ANALYSIS APPARATUS AND ROTARY VALVE

(75) Inventor: Anthony Jones, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 1018 days.

(21) Appl. No.: 13/876,911

(22) PCT Filed: Sep. 30, 2011

(86) PCT No.: PCT/GB2011/001432
§ 371 (c)(1),
(2), (4) Date: Apr. 26, 2013

(87) PCT Pub. No.: WO2012/042226
PCT Pub. Date: Apr. 5, 2012

(65) Prior Publication Data
US 2013/0217106 A1    Aug. 22, 2013

(30) Foreign Application Priority Data

Oct. 1, 2010 (GB) .................................. 1016606.4
May 31, 2011 (GB) .................................. 1109185.7

(51) Int. Cl.
*F16K 11/085* (2006.01)
*F16K 11/06* (2006.01)
(Continued)

(52) U.S. Cl.
CPC .......... *C12Q 1/6869* (2013.01); *B01L 3/5027* (2013.01); *F16K 11/085* (2013.01);
(Continued)

(58) Field of Classification Search
CPC ..... B01L 2300/0663; B01L 2300/0829; B01L 2400/0644; B01L 3/0293; B01L 3/5027;
(Continued)

(56) References Cited

U.S. PATENT DOCUMENTS 2,461,211 A    2/1949  Guthrie
3,422,848 A    1/1969  Liebman
(Continued)

FOREIGN PATENT DOCUMENTS

CN    101224320    7/2008
CN    201152237    11/2008
(Continued)

OTHER PUBLICATIONS

United Kingdom Search Report for Application No. GB1109185.7, 5 pages, dated Jun. 23, 2011.
(Continued)

*Primary Examiner* — Jennifer Wecker
(74) *Attorney, Agent, or Firm* — Wolf, Greenfield & Sacks, P.C.

(57) ABSTRACT

An analysis apparatus for performing biochemical analysis of a sample using nanopores comprises: a sensor device that supports plural nanopores, reservoirs holding material for performing the analysis; a fluidics system; and plural containers for receiving respective samples, all arranged in a cartridge that is removably attachable to an electronics unit arranged to generate drive signals to perform signal processing circuit to generate output data representing the results of the analysis. The fluidics system supplies samples selectively from the containers to the sensor device using a rotary valve.

44 Claims, 16 Drawing Sheets

(51) Int. Cl.
| | |
|---|---|
| *G01N 1/26* | (2006.01) |
| *G01N 33/53* | (2006.01) |
| *C12Q 1/68* | (2006.01) |
| *B01L 3/00* | (2006.01) |
| *G01N 33/487* | (2006.01) |
| *G01N 30/00* | (2006.01) |
| *G01N 30/02* | (2006.01) |
| *F16K 11/074* | (2006.01) |
| *G01N 33/92* | (2006.01) |
| *B01L 3/02* | (2006.01) |
| *G01N 30/60* | (2006.01) |

(52) U.S. Cl.
CPC ... *G01N 33/48721* (2013.01); *G01N 33/5306* (2013.01); *B01L 3/0293* (2013.01); *B01L 2300/0663* (2013.01); *B01L 2300/0829* (2013.01); *B01L 2400/0644* (2013.01); *F16K 11/0743* (2013.01); *G01N 1/26* (2013.01); *G01N 30/6095* (2013.01); *G01N 33/92* (2013.01); *Y10T 137/86871* (2015.04)

(58) Field of Classification Search
CPC . C12Q 1/6869; F16K 11/085; F16K 11/0743; G01N 30/6095; G01N 33/48721; G01N 33/5306; G01N 1/26; G01N 33/92; Y10T 137/86871
See application file for complete search history.

(56) References Cited

U.S. PATENT DOCUMENTS

| | | | |
|---|---|---|---|
| 3,799,411 | A | 3/1974 | Carpenter |
| 5,496,009 | A | 3/1996 | Farrell et al. |
| 5,771,935 | A | 6/1998 | Myers |
| 5,800,405 | A | 9/1998 | McPhee |
| 6,067,864 | A * | 5/2000 | Peterson ............ F16K 11/0743 137/625.18 |
| 6,537,451 | B1 | 3/2003 | Hotier |
| 6,565,535 | B2 | 5/2003 | Zaias et al. |
| 7,360,556 | B2 | 4/2008 | Mijers |
| 7,537,437 | B2 | 5/2009 | Muramatsu et al. |
| 7,766,028 | B2 | 8/2010 | Massengale et al. |
| 8,123,756 | B2 | 2/2012 | Miller et al. |
| 8,162,006 | B2 | 4/2012 | Guala |
| 9,194,504 | B2 * | 11/2015 | Cormier ............... F16K 11/0655 |
| 2001/0035516 | A1 | 11/2001 | Nichols et al. |
| 2002/0007139 | A1 | 1/2002 | Zaias et al. |
| 2003/0116206 | A1 | 6/2003 | Hartshorne et al. |
| 2005/0227239 | A1 | 10/2005 | Joyce |
| 2007/0163656 | A1 | 7/2007 | Mijers |
| 2007/0202008 | A1 * | 8/2007 | Schembri ......... G01N 33/48721 422/400 |
| 2007/0219508 | A1 | 9/2007 | Bisegna et al. |
| 2008/0003147 | A1 | 1/2008 | Miller et al. |
| 2008/0032290 | A1 | 2/2008 | Young |
| 2009/0311117 | A1 | 12/2009 | Gustafsson |
| 2010/0062446 | A1 | 3/2010 | Hanafusa |
| 2010/0070069 | A1 | 3/2010 | Hofstadler et al. |
| 2010/0113762 | A1 | 5/2010 | Ball et al. |
| 2010/0148126 | A1 | 6/2010 | Guan et al. |
| 2011/0108147 | A1 | 5/2011 | Carmody et al. |
| 2015/0031020 | A1 | 1/2015 | Jayasinghe et al. |

FOREIGN PATENT DOCUMENTS

| | | |
|---|---|---|
| DE | 202004009831 | 8/2004 |
| DE | 102006026220 B4 | 12/2007 |
| DE | 202007012680 | 1/2008 |
| DE | 102009006203 A1 | 4/2010 |
| EP | 0086073 A2 | 8/1983 |
| EP | 0247824 | 12/1987 |
| EP | 0925798 B1 | 6/1999 |
| EP | 0934757 | 8/1999 |
| EP | 1197693 A2 | 4/2002 |
| EP | 1351183 A2 | 10/2003 |
| EP | 1544310 A2 | 6/2005 |
| EP | 1640168 | 3/2006 |
| EP | 1946793 | 7/2008 |
| EP | 2163273 B1 | 3/2010 |
| EP | 2165723 A1 | 3/2010 |
| FR | 2947873 A1 | 1/2011 |
| GB | 840499 | 7/1960 |
| GB | 896056 | 5/1962 |
| GB | 2443260 | 4/2008 |
| GB | 2447043 | 9/2008 |
| GB | 2474073 | 4/2011 |
| JP | 06-319801 | 11/1994 |
| JP | 2003-235974 | 8/2003 |
| JP | 2003-328420 | 11/2003 |
| WO | WO 81/01445 | 5/1981 |
| WO | WO 03/017020 | 2/2003 |
| WO | WO 2005/005829 A1 | 1/2005 |
| WO | WO 2005/017356 A1 | 2/2005 |
| WO | WO 2005/124888 | 12/2005 |
| WO | WO 2007/054233 | 5/2007 |
| WO | WO 2007/102836 A1 | 9/2007 |
| WO | WO 2007/141058 A1 | 12/2007 |
| WO | WO 2008/008974 | 1/2008 |
| WO | 2008/111863 A1 | 9/2008 |
| WO | 2009/020682 A2 | 2/2009 |
| WO | WO 2009/077734 A2 | 6/2009 |
| WO | 2010/083147 A1 | 7/2010 |
| WO | 2011/067559 A1 | 6/2011 |
| WO | WO 2012/042226 | 4/2012 |

OTHER PUBLICATIONS

International Search Report and Written Opinion for Application No. PCT/GB2011/001432, 11 pages, dated Mar. 19, 2012.

* cited by examiner

BIOCHEMICAL ANALYSIS APPARATUS AND ROTARY VALVE

RELATED APPLICATIONS

This application is a 35 U.S.C. 371 national stage filing of International Application No. PCT/GB2011/001432 filed Sep. 30, 2011, which claims priority to British Application Nos. 1016606.4 filed Oct. 1, 2010, and 1109185.7 filed May 31, 2011. The contents of the aforementioned applications are hereby incorporated by reference.

A first aspect of the present invention relates to the performance of biochemical analysis of a sample using nanopores, for example sequencing of polynucleotides. Second to fourth aspects of the present invention relate to a rotary valve for selecting between a large number of ports.

Regarding the first aspect of the present invention, in recent years there has been considerable development of biochemical analysis of a sample using nanopores. A nanopore is a small hole in an electrically insulating layer and may be formed, for example, by protein pores or channels introduced into an amphiphilic membrane. The nanopores may allow a flow of ions to travel across the amphiphilic membrane, modulated by the nanopore on the basis of an analyte interaction, thus allowing the nanopore to provide a biochemical analysis. Various types of nanopore and analysis apparatus for using them have been developed for a range of types of biochemical analysis. One example of commercial interest is to use nanopores for sequencing of polynucleotides such as DNA. One example of an analysis apparatus for performing biochemical analysis of a sample using nanopore is disclosed in WO-2009/077734.

As such nanopores offer the potential of a platform for biochemical analysis on a commercial scale. However, in such a context it would be desirable to provide efficient handling of samples in the apparatus in order to maximise throughput and minimise costs of performing the biochemical analysis.

Regarding the second to fifth aspects of the present invention, it would be advantageous to provide a valve that is capable of selecting between a large number of ports in a wide range of applications. One example of such an application is the handling of fluids in an apparatus for performing a biochemical analysis.

One type of valve that allows selection between ports is a rotary valve comprising a stator and a rotor rotatably mounted on the stator. In a known type of rotary valve, the stator defines a plurality of first ports and a second port and the rotor has plural passages that are configured to connect different first ports to the second port as rotor rotates. This type of rotary valve provides various advantages particularly, but not exclusively for small volumes of fluid, for example allowing the valve to provide selection between the first ports with a simple construction and reliable operation.

Having regard to the third aspect of the invention, simplification of the overall construction of the rotary valve may be achieved by arranging the first ports of the stator in an annular surface that extends around the rotational axis of the rotor, facing the rotational axis. This facilitates the inclusion of relatively high numbers of first ports. However, it can be difficult to provide adequate sealing of the first ports between the stator and the rotor. This difficulty increases as the number of ports increases, and hence the overall size of the valve increases.

It would therefore be desirable to provide a valve in which these problems are alleviated.

Having regard to the third and fourth aspects of the invention, as number of first ports increases, the complexity of the network of passages in the rotor correspondingly increases. This results in increase of the size of the rotor and hence the overall size of the valve. Such an increase in size can be disadvantageous in itself in many applications where it is desired to minimise the size of the apparatus in which the valve is incorporated. Furthermore an increase in size can make it more difficult to provide sealing between the rotor and the stator.

Having regard to the fifth aspect of the invention, constructing valves for use in fluidics systems, such as systems designed within a plate, can be difficult in terms of providing a valve of simple construction that can provide and connect the desired flow paths According to a first aspect of the present invention, there is provided an analysis apparatus for performing biochemical analysis of a sample using nanopores, the analysis apparatus comprising:

a sensor device that is capable of supporting plural nanopores and being operable to perform biochemical analysis of a sample using the nanopores;

at least one reservoir for holding material for performing the biochemical analysis;

a fluidics system configured to controllably supply material from the at least one reservoir to the sensor device; and a plurality of containers for receiving respective samples, the fluidics system being configured to supply the samples selectively from the containers to the sensor device.

The analysis apparatus has a construction that encapsulates the components and material necessary to perform the biochemical analysis. In particular, the analysis apparatus incorporates the sensor device operable to perform biochemical analysis of a sample using the nanopores with at least one reservoir for holding the necessary material and a fluidics system that may supply the material to the sensor device, under suitable control. This allows for efficient performance of the biochemical analysis.

Furthermore, by providing a plurality of containers for receiving respective samples, the analysis apparatus is configured to handle multiple samples that may be introduced into the respective containers. As the fluidics system is configured to supply the samples selectively from the containers to the sensor device, the analysis apparatus provides for sequential processing and easy manipulation of the multiple samples. This allows the efficient handling of multiple samples, allowing work flows to be improved. This in turn allows a reduction of the overall cost of performing the biochemical analysis per sample.

The fluidics system may be configured to supply the samples selectively from the containers to the sensor device by including a rotary valve according to any of the second to fourth aspects of the invention as discussed below. In this case, any features of the valves in accordance with the second to fourth aspects of the invention may be combined with any features of the first aspect of the invention in any combination.

Advantageously, the analysis apparatus comprises:

a body on which the analysis apparatus, the at least one reservoir and the fluidics system are mounted, and a container element that is separate from the body and attachable thereto, the plurality of containers being formed in the container element.

As the container element is a separate element, the introduction of the samples into the containers may be performed before attachment to the body of the analysis apparatus. This facilitates the filling of the containers, improving the efficiency of the filling operation.

Furthermore, as the container element is a separate element, it may be a disposable element, allowing convenient re-use of the analysis apparatus by filling and attaching a new container element.

For example, the container element may be a well plate, the containers being wells formed in the well plate. In this case, the well plate may be filled using existing plate-based parallel manipulation techniques that are intrinsically efficient.

Optionally, the plurality of containers comprises 24 containers or more. When processing a large number of samples, such as 24 or over, it becomes less practical to provide an individual system for processing each sample, and so an integrated fluidics approach becomes preferable. Typically the plurality of containers is provided as a 96 well plate.

Optionally, the analysis apparatus, further comprises a controller configured to measure a performance target of the biochemical analysis and control the analysis to meet the performance target. The controller can be configured to control the analysis to utilise a selection of the plurality of containers in sequence, the selection of the plurality containers containing the same sample, until the performance target is met. By providing the analysis apparatus with multiple versions of the same sample, the analysis can be controlled to use several samples of the same type, if required, or to ignore wells containing a sample for which an analysis has been successfully performed. As a result, if a particular analysis becomes unexpectedly lengthy, the analysis can continue for the required length of time, but without needlessly processing every sample provided.

Optionally, the analysis apparatus is a cartridge for cooperation with another device. As such, the analysis apparatus can be disposable, or at least replaceable.

According to a second aspect of the present invention, there is provided a rotary valve comprising:

a stator defining a plurality of first ports in an annular surface that extends around a rotational axis, facing the rotational axis, and a second port; and a rotor mounted on the stator for rotation about the rotational axis inside a liner arranged between the annular surface of the stator and an annular surface of the rotor that faces the annular surface of the stator, the liner being made of a material having a greater compliance than the rotor and than the stator, the rotor having a passage extending from a first port defined in the annular surface of the stator and being in communication with the second port of the stator, the liner having at least one channel extending through the liner between the annular surface of the stator and the annular surface of the rotor and capable of providing communication between the first port of the rotor and any one of the plurality of first ports of the stator, depending on the rotational position of the rotor.

The rotary valve incorporates the first ports of the stator in an annular surface that extends around the rotational axis of the rotor, facing the rotational axis, thereby simplifying the overall construction and facilitating the inclusion of relatively high numbers of ports. Sealing is achieved by providing a liner arranged between the annular surface of the stator and a facing, annular surface of the rotor. At least one channel extending through the liner between the annular surface of the stator and the annular surface of the rotor provides communication between the first port of the rotor and any one of the plurality of first ports of the stator, depending on the rotational position of the rotor. The liner is made of a material selected to have a greater compliance than the rotor and than the stator. This makes it easier to provide the required degree of sealing. Without the liner, the sealing is directly between the facing annular surfaces of the rotor and stator, in which case there is difficulty in selecting materials that provide sufficient sealing whilst maintaining the other desired mechanical properties for operation of the valve, for example sufficient rigidity and sufficiently low resistance. The difficulty in sealing directly between the facing annular surfaces of the rotor and stator increases as the number of ports increases, so the present invention facilitates the formation of valves with relatively high numbers of ports.

The rotary valve may be advantageously applied to the handling of small volumes of fluid, in which the difficulty in sealing is worse, for example in which the ports of the stator and the rotor, the passage of the rotor and the at least one channel of the liner have cross-sectional areas of no more than 10 $mm^2$, preferably no more than 1 $mm^2$. In one advantageous use of the rotary valve, the stator is on a body that is arranged to allow attachment of a well plate comprising a plurality of wells corresponding to the plurality of first ports, the body defining channels connecting the wells to the corresponding first ports.

In one advantageous construction, the passage extends to a second port defined in the rotor that is positioned on the rotational axis and is in communication with the second port of the stator. In this construction, the same passage is always connected to the second port and provides communication with any one of the first ports selected by the rotational position of the rotor. Such selective connection of any one of the first ports to the second port is achieved using a very simple configuration that is relatively compact and is scalable to any number of first ports. The first ports need merely to be spaced around the rotational axis, so increasing the number of second ports only increases the size marginally. In approximate terms, the circumference and hence diameter of the rotary valve scales linearly with the number of first ports. The size is much reduced as compared to providing the rotor with respective passages for connecting each first port to the second port.

The passage in the rotor may communicate with a passage in the liner that is in communication with the second port of the stator. In this configuration, the liner is also used to seal the connection between the rotor and the second port of the stator.

According to a third aspect of the present invention, there is provided a rotary valve comprising:

a stator; and a rotor rotatably mounted on the stator for rotation about a rotational axis;

the stator defining a plurality of first ports arranged around the rotational axis and a second port, the rotor defining a first port capable of communication with any one of the first ports of the stator depending on the rotational position of the rotor, a second port positioned on the rotational axis and in communication with the second port of the stator, and a passage extending between the first port and the second port.

This rotary valve achieves selective connection of any one of the first ports to the second port using a very simple configuration. Selection of the first ports is achieved by rotation of the rotor, but, as the second port is positioned on the rotational axis, the second port of the stator and the second port of the rotor remain in communication as the rotor rotates. This provides a simple configuration for the valve and allows for sealing between the second port of the stator and the second port of the rotor. This configuration is relatively compact and is scalable to any number of first ports. The first ports need merely to be spaced around the rotational axis, so increasing the number of second ports only increases the size marginally. In approximate terms, the circumference and hence diameter of the rotary valve scales linearly with the number of first ports. The size is much reduced as compared to providing the rotor with respective passages for connecting each first port to the second port.

Such a rotary valve may be advantageously applied to the handling of small volumes of fluid, for example in which the first ports, the passage, the collection chamber and the second port have cross-sectional areas of no more than 10 mm$^2$, preferably no more than 1 mm$^2$. In one advantageous use of the rotary valve, the stator is on a body that is arranged to allow attachment of a well plate comprising a plurality of wells corresponding to the plurality of first ports, the body defining channels connecting the wells to the corresponding first ports. According to a fourth aspect of the present invention, there is provided a rotary valve comprising: a stator; and a rotor rotatably mounted on the stator for rotation about a rotational axis;

the stator defining a plurality of first ports arranged around the rotational axis facing the rotor;

the valve comprising a collection chamber extending in at least part of an annulus around the axis of rotation of the valve member, the stator defining a second port in communication with the collection chamber, and the rotor providing a passage extending between the collection chamber with which the passage is in communication and a position where the passage is capable of communication with any one of the plurality of first ports depending on the rotational position of the rotor.

The rotary valve includes a collection chamber that extends in at least part of an annulus around the axis of rotation, and the first ports are also arranged around the rotational axis. As a result of this configuration of the collection chamber and the first ports, it is possible for the rotor to be arranged with a passage that can connect the collection chamber to any selected one of the plurality of first ports depending on the rotational position of the rotor. As the collection chamber is in communication with the second port, this results in the selected first port also being connected to the second port.

Such selective connection of any one of the first ports to the second port is achieved using a very simple configuration of the collection chamber and the passage in the rotor. This configuration is relatively compact and is scalable to any number of first ports. The first ports need merely to be spaced around the rotational axis, so increasing the number of second ports only increases the size marginally. In approximate terms, the circumference and hence diameter of the rotary valve scales linearly with the number of first ports. The size is much reduced as compared to providing the rotor with respective passages for connecting each first port to the second port.

Such a rotary valve may be advantageously applied to the handling of small volumes of fluid, for example in which the first ports, the passage, the collection chamber and the second port have cross-sectional areas of no more than 10 mm$^2$, preferably no more than 1 mm$^2$. In one advantageous use of the rotary valve, the stator is on a body that is arranged to allow attachment of a well plate comprising a plurality of wells corresponding to the plurality of first ports, the body defining channels connecting the wells to the corresponding first ports.

In one advantageous construction, the rotor and the stator have interfacing contact surfaces that extend transversely, preferably perpendicular, to the rotational axis, the plurality of first ports and the second port opening in the contact surface of the stator. With this construction, sealing of the interfacing contact surfaces may be facilitated by constructing the valve to apply a high load between the rotor and stator along the rotational axis. This makes sealing easier than if the ports are provided in interfacing contact surfaces extending parallel to the rotational axis.

For example, the loading may be achieved by the valve further comprising a biasing arrangement arranged to bias the rotor against the stator, for example including a resilient biasing element engaging the rotor.

According to a fifth aspect of the invention, there is provided a rotary valve comprising: a stator defining a plurality of first ports, and a second port, a rotor mounted on the stator for rotation about a rotational axis, the valve comprising a passage being in communication with the second port of the stator and extending to a position for communicating with any one of the plurality of first ports of the stator individually, depending upon the rotational position of the rotor.

According to this arrangement, it is possible for the rotor to simply connect the passage of the valve to the desired first port of the stator. As a result, the stator can be formed directly in the plate of a fluidics system, and the rotor can provide the means for connecting the desired ports formed in the plate.

Optionally, the first ports, the passage, and the second port have cross-sectional areas of no more than 10 mm$^2$, preferably no more than 1 mm$^2$.

Optionally the rotary valve can further comprise a liner arranged between the rotor and the stator, wherein the liner is fixed relative to the rotor. The liner can optionally be a made of a material more compliant than both the stator or rotor. The provision of the liner in fixed relation to the rotor allows for an improved seal between the stator and rotor.

In the hereinafter described embodiments, the second and third aspects of the present invention are implemented in combination in a rotary valve. However, this is not essential. A rotary valve in accordance with the second aspect of the invention may be implemented in combination with the fourth aspect of the invention, with the second port of the rotor communicating with the collection chamber.

Embodiments of the present invention will now be described by way of non-limitative example with reference to the accompanying drawings, in which.

Figure 1:
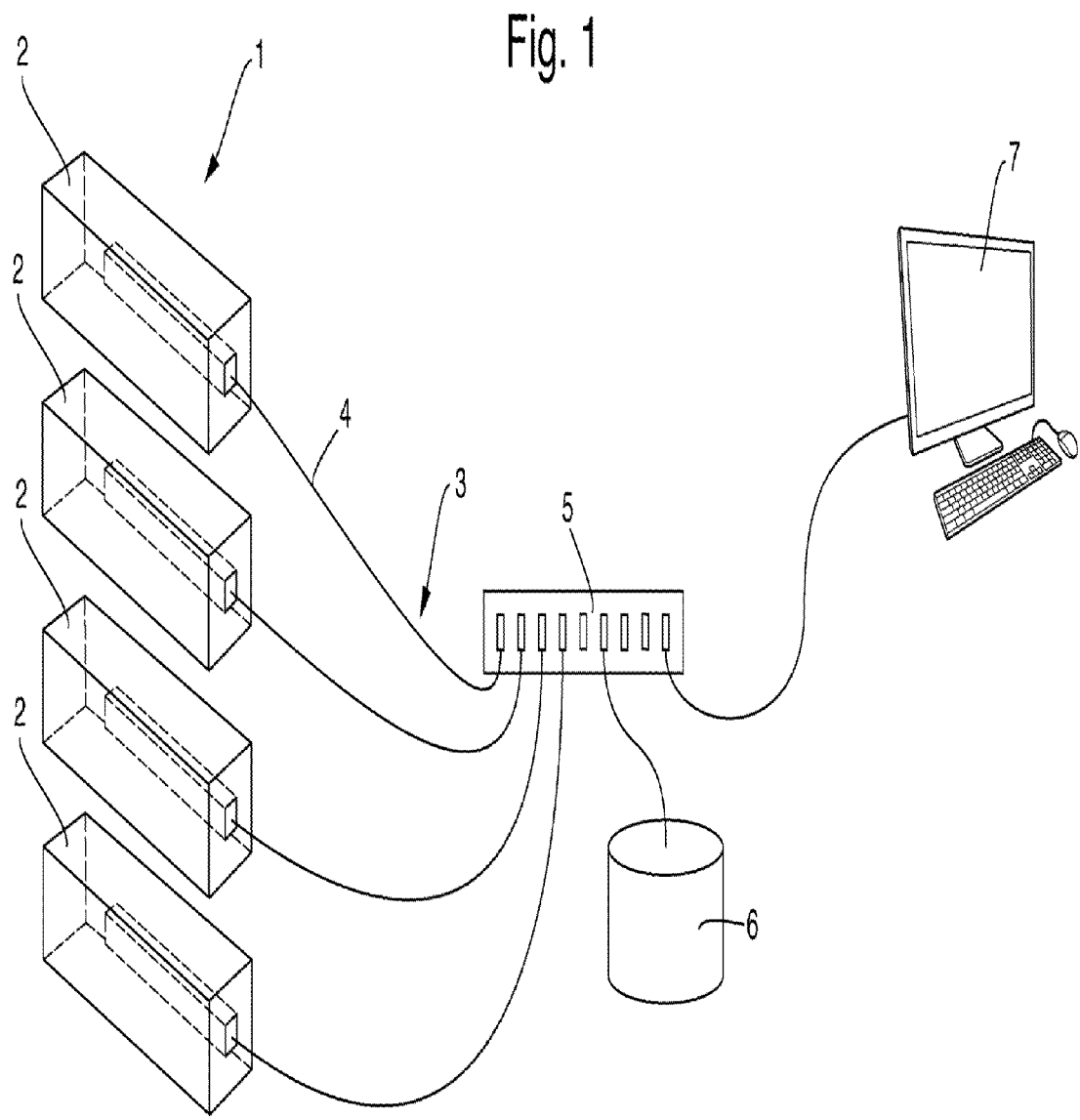
FIG. 1 is a schematic view of a biochemical analysis instrument.

There will first be described an instrument for performing biochemical analysis using nanopores in the form of protein pores supported in an amphiphilic membrane, but this is not limitative of the invention.

The instrument 1 is formed a plurality of modules 2 that are each connected to a data network 3. In this example, the network 3 is formed as a conventional local area network by each module 2 being connected by a cable 4 to a network switch 5. In general, the modules 2 may be connected to any type of data network, including wireless networks, wide-area networks and the internet Attached to the network 3, there may also be a storage device 6 of any type, for example a NAS, and an external computer 7 that is used to address the modules 2 and may be a conventional computer having an HTTP browser.

Due to the networked configuration of the instrument 1, any number of modules 2 may be provided in a given location, depending on the local requirements, for example from a small number of modules 2 or even a single module 2 in a small-scale research facility to a large bank of modules 2 in a commercial sequencing centre. Similarly the modules 2 need not be physically close and so the instrument 1 may be formed from modules 2 that are distributed in different locations, even different countries.

An individual module 2 will now be described.

Figure 2:
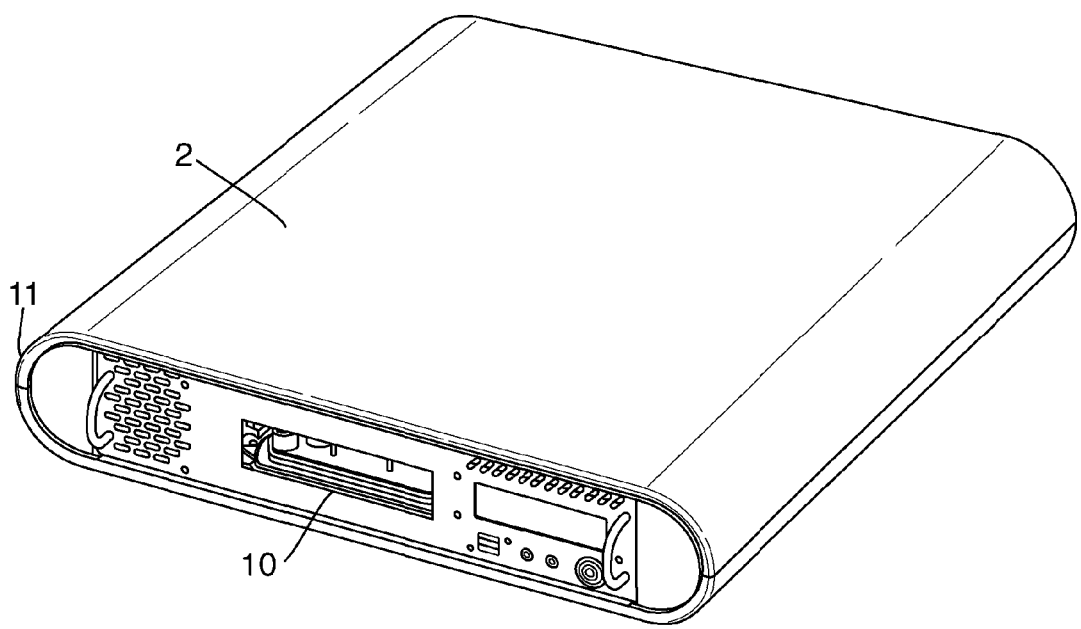
FIG. 2 is a perspective view of a module of the instrument.
Figure 3:
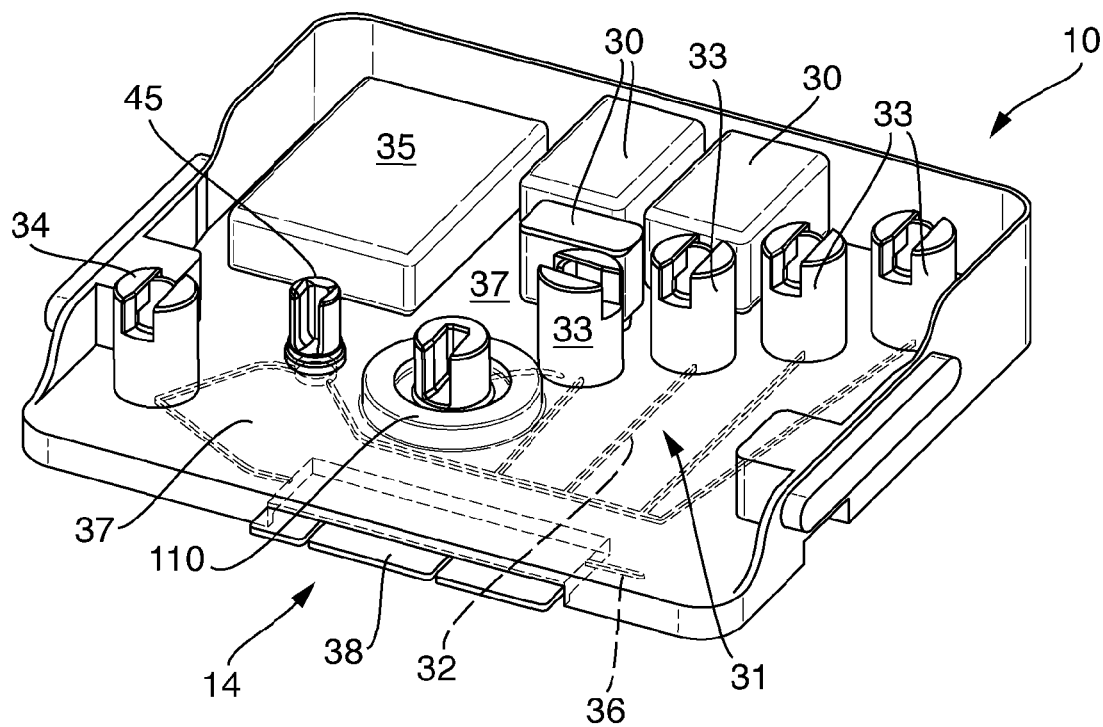
FIG. 3 is a perspective view from above of a cartridge that is replaceable in the module.

As shown in FIG. 2, the module 2 has a cartridge 10 that is replaceable in the housing 11 of the module 2. The cartridge 10 forms an analysis apparatus for performing a biochemical analysis as will now be described. The cartridge 10 has a construction shown in FIG. 3.

Figure 4:
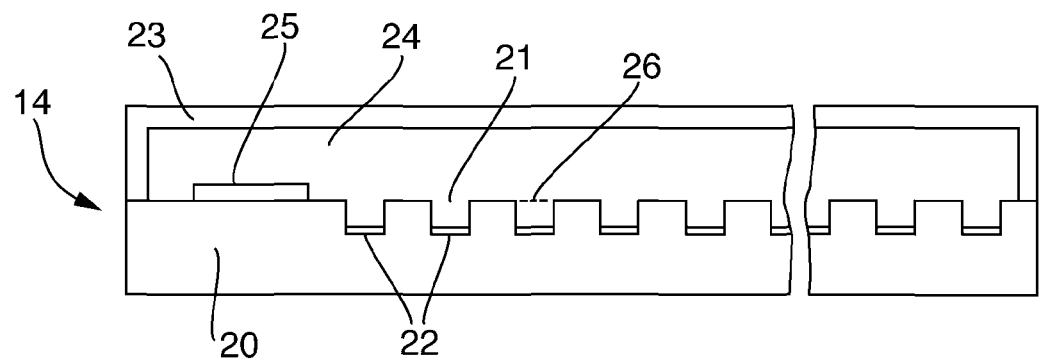
FIG. 4 is a cross-sectional view of a part of a sensor device of the cartridge.

The cartridge 10 comprises a body 37 formed for example of moulded plastic. The body 37 of the cartridge 10 mounts a sensor device 14 that is an apparatus as described in detail in WO-2009/077734 which is incorporated herein by reference. Without limitation to the generality of the teaching therein, the sensor device 14 has a construction as shown in cross-section in FIG. 4 comprising a body 20 in which there is formed a plurality of wells 21 each being a recess having a well electrode 22 arranged therein. A large number of wells 21 is provided to optimise the data collection rate. In general, there may be any number of wells 21, although only a few of the wells 21 are shown in FIG. 4. In one example, the number of wells is 256 or 1024, but there could be one, two or three orders of magnitude more. The body 20 is covered by a cover 23 that extends over the body 20 and is hollow to define a chamber 24 into which each of the wells 21 opens. A common electrode 25 is disposed within the chamber 23.

The sensor device 14 is prepared to form an amphiphilic membrane 26, such as a lipid bilayer, across each well 21 and to insert nanopores that are protein pores into the amphiphilic membrane 26. This preparation is achieved using the techniques and materials described in detail in WO-2009/077734, but may be summarised as follows. Aqueous solution is introduced into the chamber 24 to form the amphiphilic membrane 26 across each well 21 separating aqueous solution in the well 21 from the remaining volume of aqueous solution in the chamber 24. Protein pores are provided into the aqueous solution, for example by being introduced into the aqueous solution before or after that is introduced into the chamber 24 or by being deposited on an internal surface of the chamber 24. The protein pores spontaneously insert from the aqueous solution into the amphiphilic membranes 26.

A protein pore is an example of a nanopore and may be used to perform a biochemical analysis, as follows. In respect of any given well 21, when an amphiphilic membrane 26 has been formed and a protein pore is inserted therein, the well 21 is capable of being used as a sensor element to sense interactions between molecular entities and the protein pore that are stochastic physical events because the output electrical signal across the amphiphilic membrane 26 is dependent on those interactions in that the interactions cause characteristic changes therein. For example, there will typically be interactions between the protein pore and a particular molecular entity (analyte) that modulate the flow of ions through the pore, creating a characteristic change in current flow through the pore. The molecular entity may be a molecule or part of a molecule, for example a DNA base. Thus the interaction appears as a characteristic event in the electrical signal across the protein pore in each amphiphilic membrane 26.

The electrical signals may be detected as the signals between the well electrodes 22 and the common electrode 25, and may subsequently be analysed to produce output data representing the results of the biochemical analysis. Separate electrical signals are derived from the protein pores in the amphiphilic membranes 26 in different wells 21, each resulting in a different channel of the output data.

A wide range of types of biochemical analysis may be performed. One such biochemical analysis is sequencing of polynucleotides. In this case, the electrical signal is modulated differently for each different base, allowing discrimination thereof.

The body 37 of the cartridge 10 encapsulates the components and material necessary to perform the biochemical analysis and is capable of preparing the sensor device 14 automatically. For this purpose, the cartridge 10 mounts reservoirs 30 containing sufficient volumes the necessary materials, such as buffer solutions, lipids, protein pores (in solution), pre-treatment (if required), and sample, such that many 'refreshes' of the analysis apparatus are possible. Thus the cartridge 10 is fully self-contained in that all reagents and other materials required for the biochemical analysis are present and may be used for sample preparation. The cartridge 10 mounts a waste reservoir 35 for disposal of waste products from the sensor device 14.

The body 37 of the cartridge 10 also mounts a fluidics system 31 for supplying the fluids from the reservoirs 30 to the sensor device 14. The fluidics system 31 includes supply channels 32 and inlet pumps 33 for pumping fluids from the reservoirs 30 to the sensor device 14. The fluidics system 31 also includes an output pump 34 for pumping fluids out of the sensor device 14 through an outlet channel 36 connected to the waste reservoir 35 for disposal of the fluids. The pumps 33 and 34 may be syringe pumps depending on volume and flow rate required (for example as supplied by Hamilton Company, Via Crusch 8, Bonaduz, GR, Switzerland CH-7402).

The fluidics system also includes a selector valve 45 disposed in the supply channels 32 between the inlet pumps 33 connected to the reservoirs 30 and the output pump 34. The selector valve 45 selectively connects the sensor device 14 to the reservoirs 30 or to the waste reservoir 35. The waste reservoir 35 is open to atmosphere.

One of the reservoirs 30 holds the lipid and the fluidics system 31 supplies the lipid to the sensor device 14 in the same manner as the other materials. As an alternative for supplying the lipid, the supply channels 32 of the fluidics system 31 may pass into the sensor device 14 through a lipid assembly holding lipid so that the fluid flowing into the sensor device 14 acquires lipid and introduces it into the sensor device 14.

The pumps 33 and 34 may thus be operated to control the flow of fluids to prepare the sensor device 14 to form an amphiphilic membrane 26 across each well 21 and to insert nanopores that are protein pores into the amphiphilic membrane 26, as discussed above.

Figure 11:
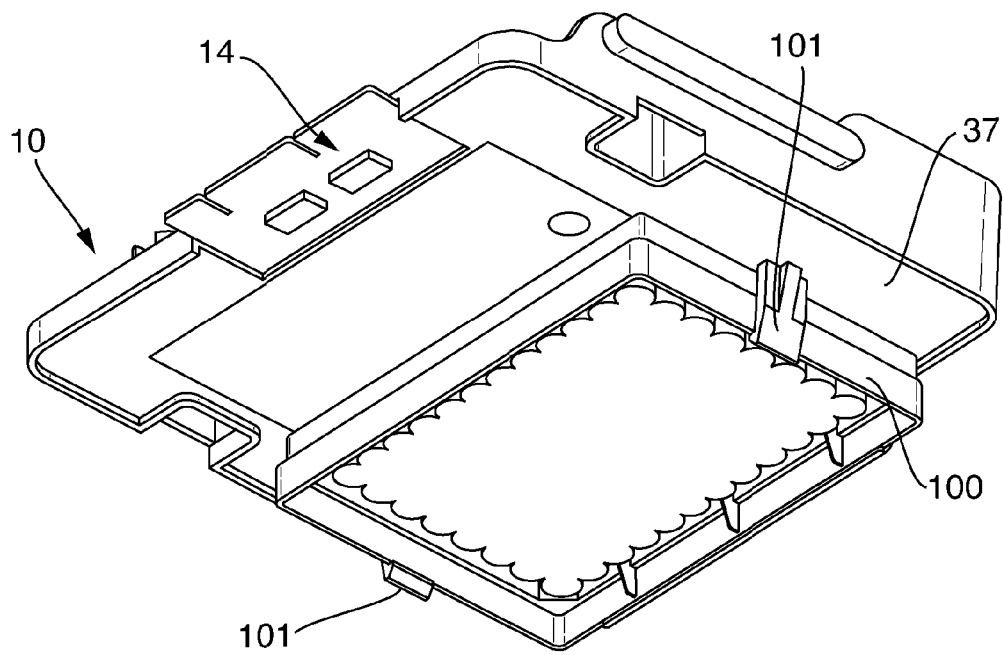
FIGS. 11 and 12 are perspective views from below of the cartridge, showing a well plate, respectively, attached and separated.
Figure 12:
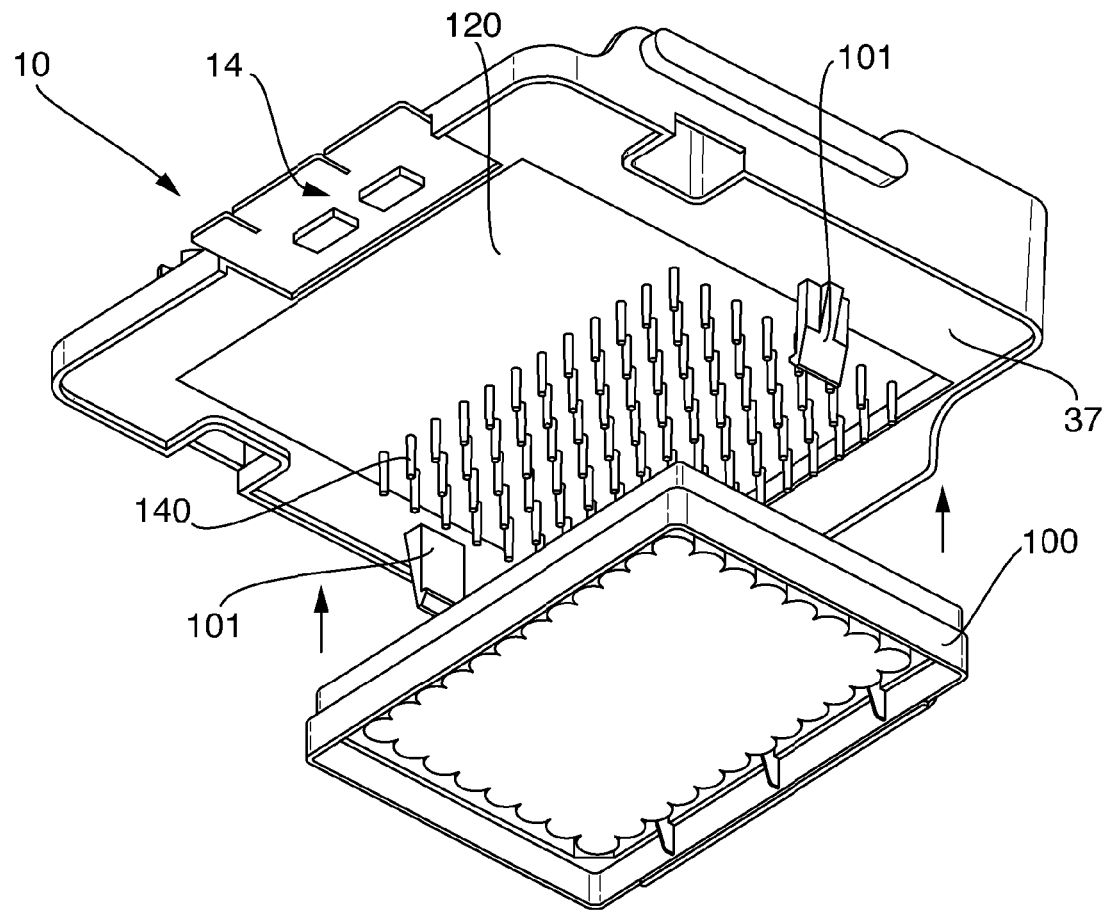

The cartridge 10 is capable of receiving a plurality of samples as follows. As shown in FIG. 11, the body 37 of the cartridge 10 is arranged to allow attachment of a well plate 100. In particular, the body 37 has a pair of clips 101 protruding from its underside and to which a well plate 100 may by attached by pressing the well plate 100 against the clips 101 in the direction of the arrows in FIG. 12.

Figure 13:
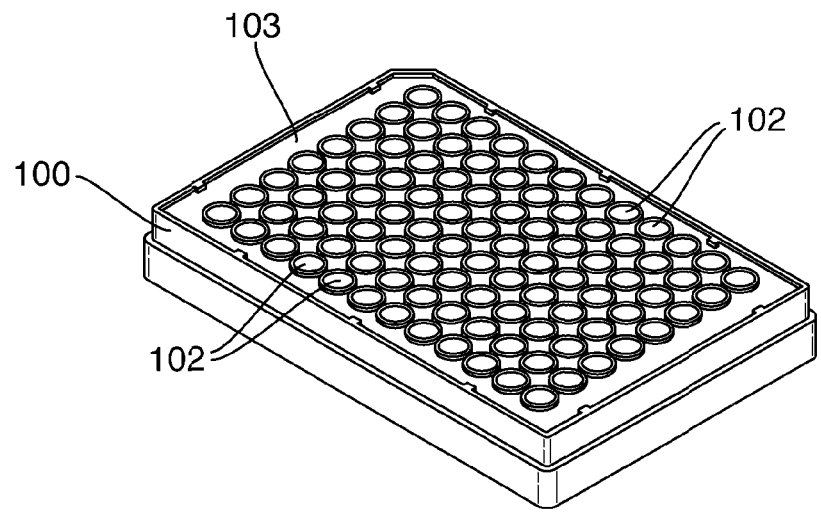
FIG. 13 is a sectioned perspective view of part of the well plate.
Figure 14:
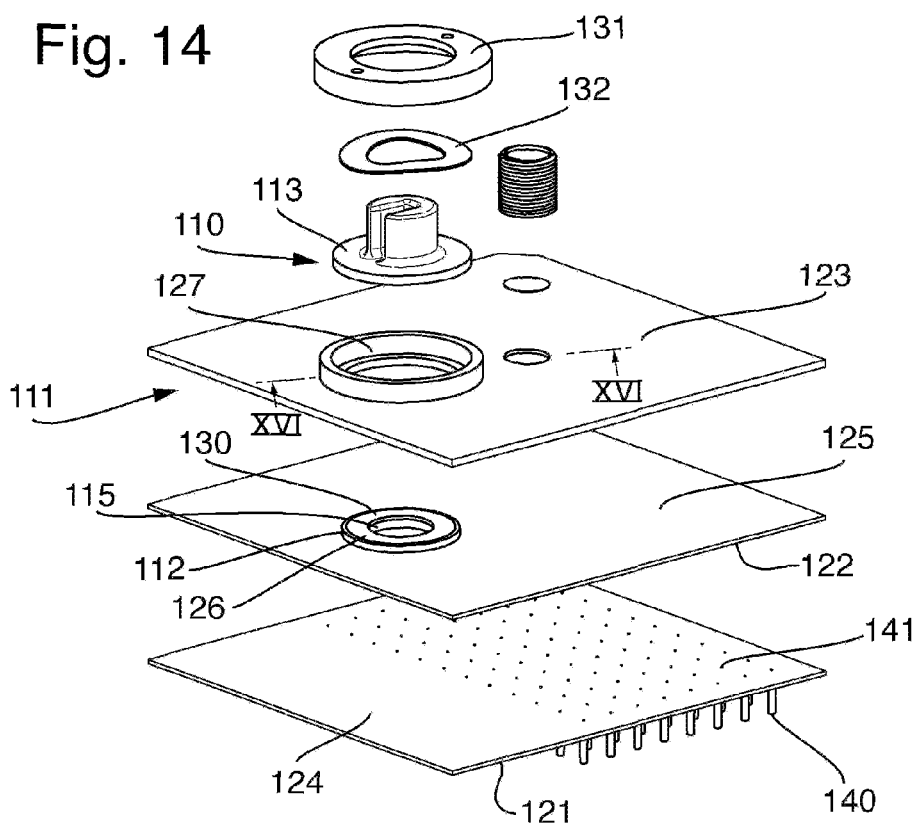
FIGS. 14 and 15 are perspective views from above and below respectively of a valve assembly incorporating a valve of a first construction.
Figure 15:
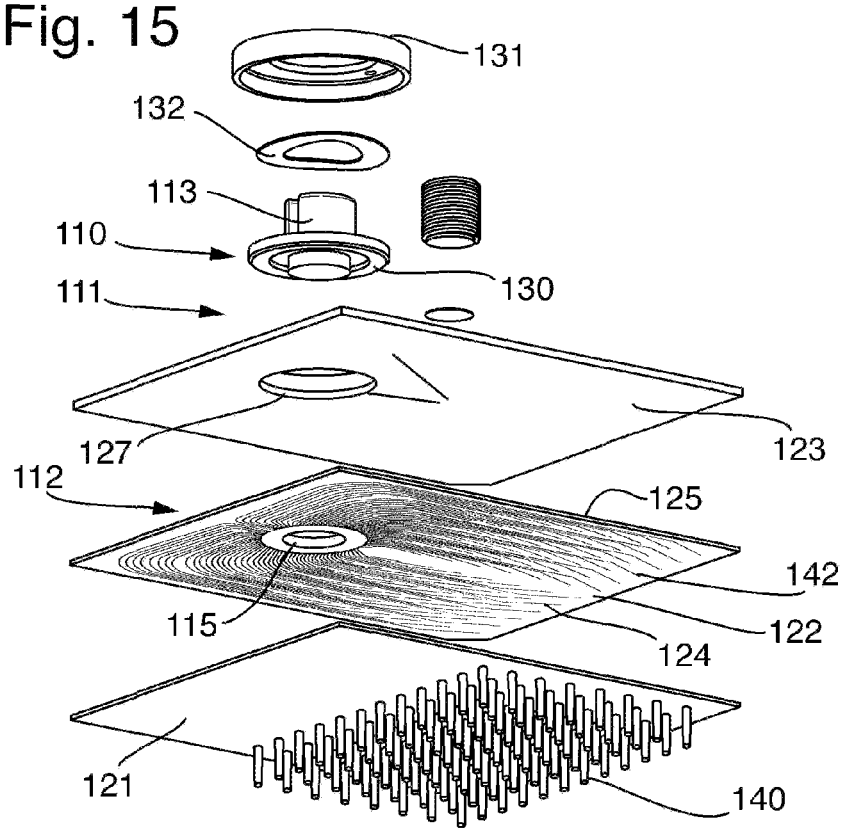

As shown in FIG. 13, the well plate 100 is of standard construction and forms a plurality of wells 102 opening a flat upper surface 103 of the well plate 100. In this example the well plate 100 has 96 wells 102, but in general may have any number of wells 102. Preferably, the plate has at least 24 wells 102, more preferably at least 48 wells 102. The plate can have at least 96 wells, at least 384 wells or even at least 1536 wells 102. The wells 102 are used as containers for receiving respective samples. In use, the samples are introduced into the respective wells 102 before attachment of the well plate 102 to the cartridge 10 and before loading of the cartridge 10 into the module 2. The well plate 102 may be filled with samples using known plate-based parallel manipulation techniques that are intrinsically efficient. As the well plate 100 is a separate element from the body 37 of the cartridge 10 it is easily filled prior to attachment facilitates the filling of the wells 102. More generally, similar advantages could be achieved by replacing the well plate 100 by any other type of container element comprising a plurality of containers that might be wells or closed containers.

After introduction of the samples, the well plate 100 is attached to the cartridge 10 with the flat upper surface 103 against the body 37, to encapsulate the well plate 100 into the cartridge 10. Subsequently, the cartridge 10 is loaded into the module 2.

The fluidics system 31 is configured to supply the samples selectively from the wells 102 to the sensor device 14, using a valve 110 that is a rotary valve. Two possible constructions for the valve 110 will now be described.

In the first possible construction in accordance with the fourth aspect of the invention, the valve 110 is formed in a valve assembly 111 illustrated in FIGS. 14 to 21 that is incorporated into the body 37 of the cartridge 10.

The valve 110 comprises a stator 112 and a rotor 113. The stator 112 is provided on a body 120 formed by a first plate 121, a second plate 122 and a third plate 123 that are fixed together by interfacing contact surfaces 124 between the first and second plates 121 and 122 and by interfacing contact surfaces 125 between the first and second plates 122 and 123.

The rotor 113 is rotatably mounted on the stator 112 for rotation about a rotational axis R. A bearing for the rotational mounting is provided by the rotor 113 comprising a bearing stub 114 that is mounted in a bearing recess 115 formed in the stator 112. In particular, the bearing stub 114 is has a length chosen to provide a clearance between the end of the bearing stub 115 and the first sheet 121. Around the bearing recess 115, the second sheet 122 has an annular boss 126 that protrudes towards the first sheet 121 and the stator 113, the second sheet 123 having a circular aperture 127 in which the annular boss 126 fits.

In addition the bearing for the rotational mounting is provided by the rotor 113 comprising a disc 116 having a cylindrical outer surface 117 that is mounted in an annular wall 118 formed in the stator 112 and protruding therefrom, in particular from the third plate 123 outside the circular aperture 127. Alternatively, there may be a clearance gap between the disc 116 and the annular wall 118.

The stator 112 and rotor 113 have interfacing contact surfaces 130 that are annular and extend perpendicular to the rotational axis R, being provided as follows. The contact surface 130 of the rotor 113 is formed by a lower surface of the disc 116 that extends perpendicular to the rotational axis R both overlapping the annular boss 126 of the second plate 122 and overlapping the third plate 123 outside the aperture 127. Thus the contact surface 130 of the stator 112 is formed by the adjacent parts of the upper surface of the annular boss 126 of the second plate 122 and the upper surface of the third plate 123, which are flush with each other.

Sealing of the interfacing contact surfaces 130 of the stator 112 and the rotor 113 is facilitated by applying a load between the stator 112 and the rotor 113 along the rotational axis R. This is achieved by a biasing arrangement arranged as follows to bias the rotor 113 against the stator 112. A clamping ring 131 is attached to the stator 113, in particular screwed to the annular wall 118. A disc spring 132 is disposed between and engages the clamping ring 131 and the rotor 112. The disc spring 132 provides resilient biasing between the stator 112 and the rotor 113, although could be replaced by another type of resilient biasing element.

Figure 17:
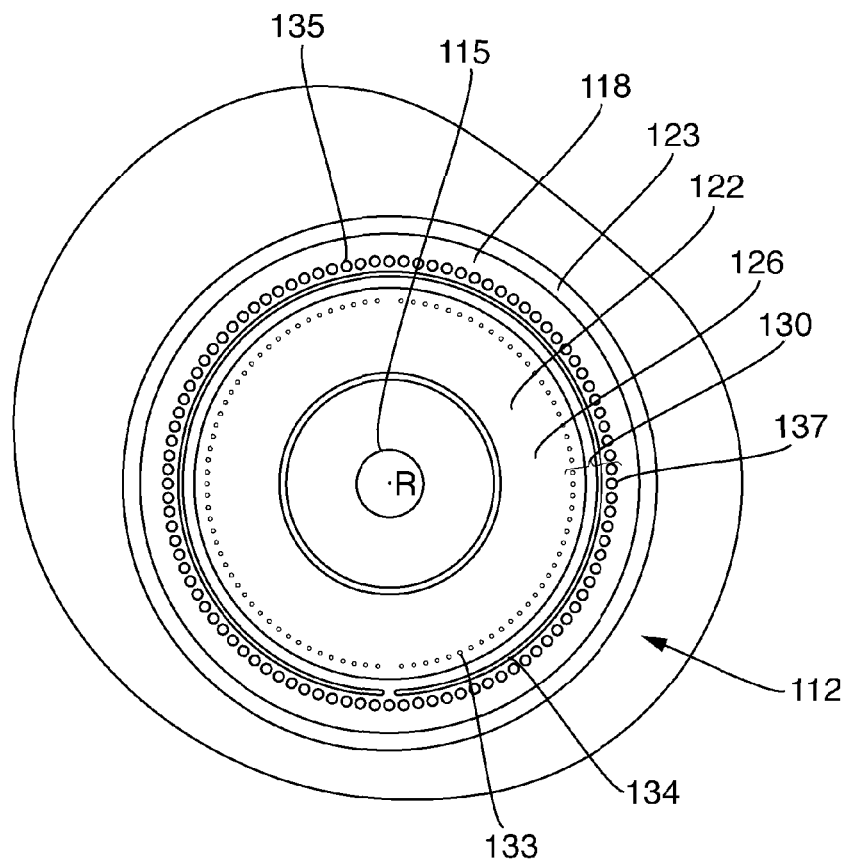
FIG. 17 is a partial plan view from above of a body of the valve assembly around a stator of the valve of the first construction.
Figure 18:
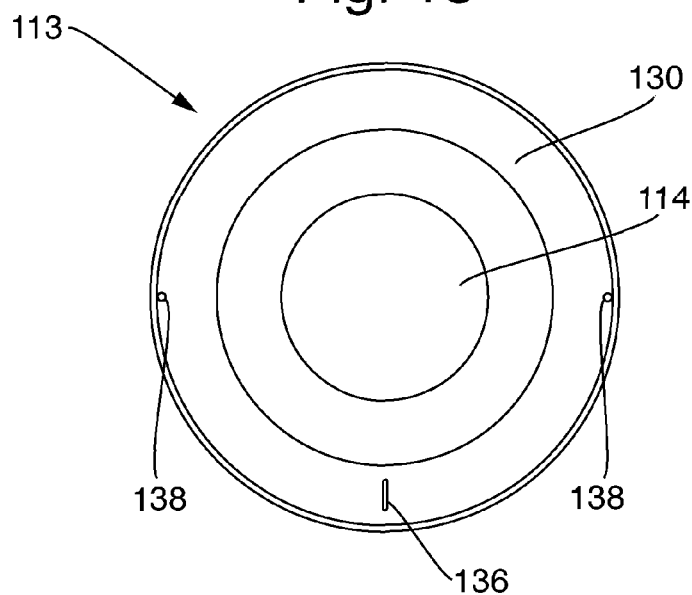
FIG. 18 is a plan view from below of a rotor of the valve of the first construction.

The contact surface 130 of the stator 112 is arranged as shown in FIG. 17 which is a plan view of the stator 112 without the clamping ring 131. In particular, a plurality of inlet ports 133 are formed in the contact surface 130 of the stator 112 arranged in a circle around the rotational axis R. In this example, the valve 110 has 96 inlet ports 233 but in general the valve 110 may have any number of ports 233. Preferably, the valve has at least 24 inlet ports 233 and more preferably at least 48 inlet ports 233. The valve can have at least 96 ports, at least 384 ports or even at least 1536 ports 233. The inlet ports 133 are evenly spaced, except for a gap at one position, lowermost in FIG. 17. The inlet ports 133 are formed in particular in the upper surface of the annular boss 126 of the second plate 122, facing the contact surface 130 of the rotor 113.

Also, a collection chamber 134 is formed in the contact surface 130 of the stator 112. The collection chamber 134 is formed as a groove in the upper surface of the third plate 122, facing the contact surface 130 of the rotor 113. The collection chamber 134 extends outside the inlet ports 133 in a circular annulus around the rotational axis R aligned angularly with the inlet ports 133, that is with a gap aligned angularly around the rotational axis R with the gap in the inlet ports 133.

The stator 112 further includes an outlet port 135 in communication with the collection chamber 134 by being formed in the lower surface of the collection chamber 134.

The rotor 113 is provided with a passage 136 formed as a groove in the contact surface 130 of the rotor 113. The passage 136 extends radially from the position of the inlet ports 133 to the position of the collection chamber 135. Thus, the passage 136 is capable of communication with any one of the inlet ports 133 depending on the rotational position of the rotor 113. Rotation of the rotor 113 allows different inlet ports 133 to be selected. As the collection chamber 134 is aligned angularly with the inlet ports 133, at all rotational positions where the passage 136 communicates with an inlet port 133, the passage 136 also communicates with the collection chamber 134, thereby connecting the selected inlet port 133 to the outlet port 135. Therefore, rotation of the rotor 136 selectively connects individual inlet ports 133 to the outlet port 135.

When the rotor 133 is aligned with the gap in the inlet ports 133 and the gap in the collection chamber 134, the passage 136 is closed against the contact surface 130 of the stator 112, thereby closing the valve 110. However, as an alternative, the inlet ports 133 can be brought together to omit the gap so that inlet ports are arranged in a complete annulus and the valve 110 cannot be closed.

As an alternative to forming the collection chamber 134 in the contact surface 130 of the stator 112, a similar operation could be achieved by alternatively forming the collection chamber 134 as a groove in the contact surface 130 of the rotor 113 opening into the passage 136.

To provide positioning of the rotor 112, the contact surface 130 of the stator 112 has a circular array of pits 137 at the same pitch as the inlet ports 133, and the contact surface 130 of the rotor 113 has pips 138 that fit into the pits 137. The pips 138 may be pushed out of the pits 137 on rotation of the rotor 112 but are aligned to hold the rotational position of the rotor 112 in stepped rotational positions that each locate the passage 136 in communication with each a respective inlet port 133, or in one of the stepped rotational positions to locate the passage 136 over the gap in the inlet ports 133 and the gap in the collection chamber 134.

The size of the valve 110 is minimised by arranging the inlet ports 133 as close together as possible, but the same operation could be achieved by increasing the size of the gap in the inlet ports 133 so that the inlet ports 133 extend around a smaller part of the annulus. In this case, the collection chamber 134 can be correspondingly reduced in length to extend in a shorter part of the annulus.

The body 120 defines channels connecting the wells 102 of the well plate 100 to the inlet ports 133 as follows.

Figure 19:
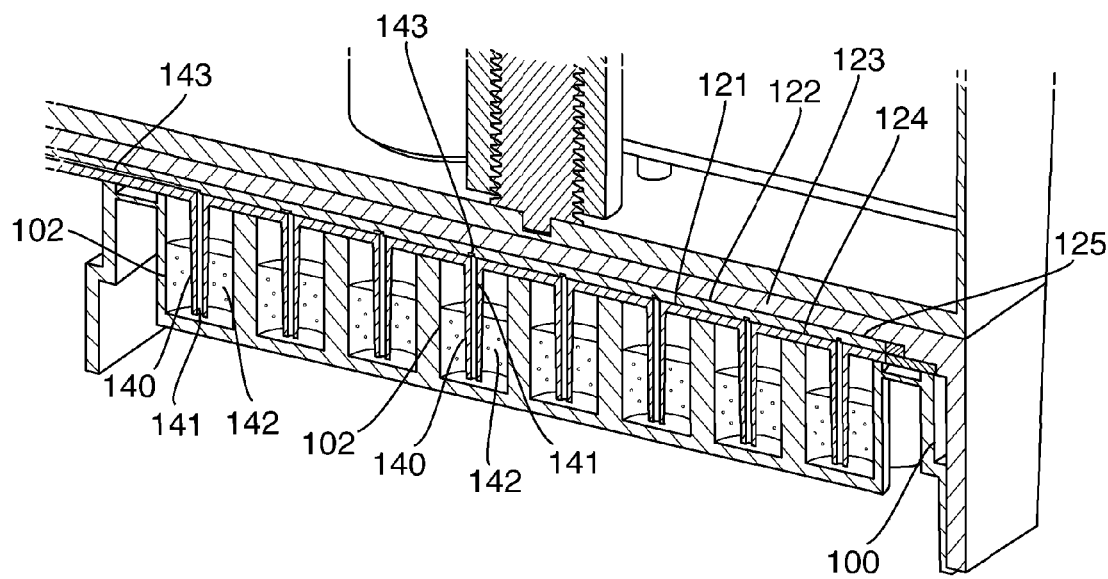
FIG. 19 is a partial cross-sectional view of the body of the valve assembly and a well of the well plate.

The first plate 121 is disposed on the underside of the cartridge 10 at the position where the well plate 100 is attached and has an array of nozzles 140 protruding outwardly and having the same spacing as the wells 102 of the well plate 100 to align therewith. As a result, when the plate 100 is attached to the cartridge 10, each nozzle 140 protrudes into a respective well, as shown in FIG. 19. Each nozzle 140 comprises a through hole 141 that extends through the nozzle 140 and through the first plate 121 to the contact surface 124 of the first plate 121 to form part of a channel in respect of the well 102.

The nozzles 140 extend into the wells 102 by a sufficient distance that the end of the nozzle 140 is submerged below the surface of a sample 142 in the well 102. In this manner, the sample 142 effectively seals the nozzle 140. This avoids the need for a hermetic seal between the well plate 100 and the first plate 121.

Figure 20:
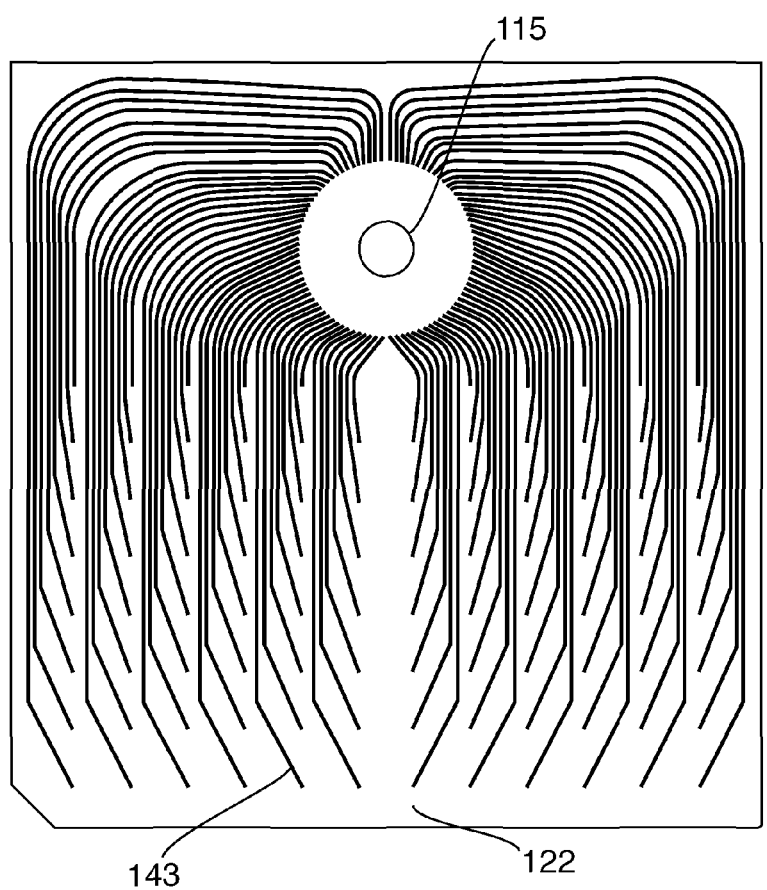
FIG. 20 is a plan view from below of a second plate of the valve assembly.

The contact surface 124 of the second plate 122 is formed with a set of grooves 143 that form part of the channel in respect of each well 102. Each groove 143 communicates at one end with the through hole 141 that extends through the nozzle 140 and through the first plate 121. As shown in FIG. 20, the grooves 143 extend from the nozzles 140 to the stator 112, in particular to the annular boss 126 on the opposite side of the second plate 122 from the outlet ports 133. The remainder of the channels are formed by through holes 144 extending through the boss 126 of the second plate 122 from a respective groove 144 in the contact surface 124 of the second plate 122 to a respective inlet port 133.

Figure 16:
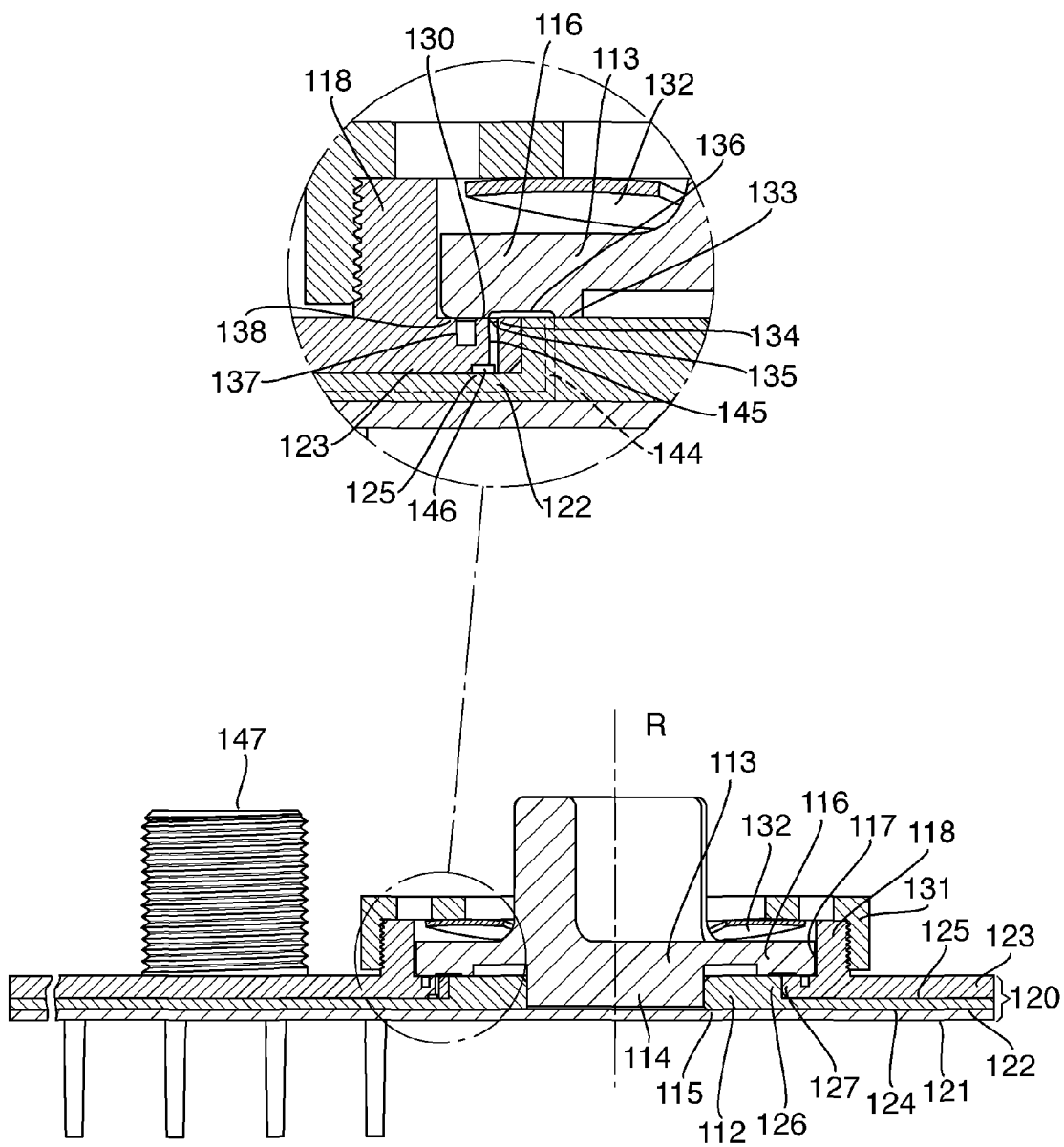
FIG. 16 is a cross-sectional view through the valve assembly of FIG. 14 taken along line XVI-XVI.

The body 120 also defines a channel connecting to the outlet port 135 as follows. The third plate 123 has a through hole 145, shown in dotted outline in FIG. 16, that extends from the outlet port 135 through the third plate 123 to the contact surface 125 of the third plate 123, forming part of the channel. The remainder of the channel is formed by a groove 146 in the contact surface 125 of the third plate 123 extending away from the through hole 145. As shown in FIG. 16, the groove 146 extends to a dosing pump 147 operable to pump a sample from a well 102 selected by the rotational position of the valve 110 through the valve 110 to the sensor device 14.

The first, second and third plates 121-123 may be formed from any suitable material that provides sealing for channels defined between the contact surfaces 124 and 125. Suitable materials include PMMA (poly(methyl methacrylate)), PC (polycarbonate) or COC (cyclic olefin co-polymer). The first, second and third plates 121-123 may be sealed by any suitable technique for example ultrasonic welding, laser welding or bonding. PMMA is particularly effective due to the ability to use PMMA diffusion bonds. The first, second and third plates 121-123 may be injection moulded.

Similarly, the rotor 113 may be formed from any suitable material that provides sealing and sufficiently low friction for rotation. One suitable material is PTFE (polytetrafluoroethylene) that may be machined with a section made of an elastomer (e.g. silicone) to provide compression. PTFE can lower the torque required for rotation and has good sealing properties. The elastomer allows the rotor 112 to be clamped but still rotate. Alternatively the rotor 113 can be made from a material that can be injection moulded, for example, FEP (fluorinated ethylene propylene) or UHMWPE (ultra-high-molecular-weight polyethylene).

Figure 22:
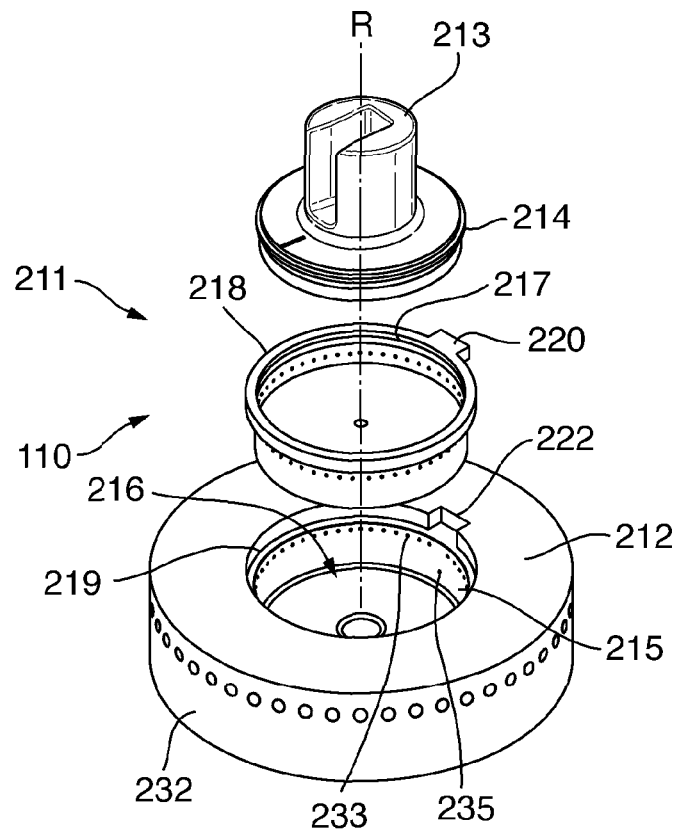
FIG. 22 is an exploded perspective view from above of a valve assembly incorporating a valve of a second construction.
Figure 23:
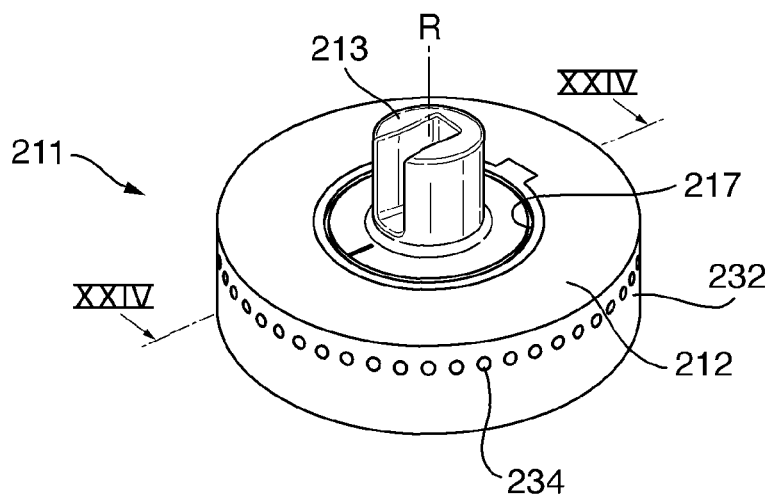
FIG. 23 is perspective view from above of the valve assembly of FIG. 22 in an assembled state.
Figure 24:
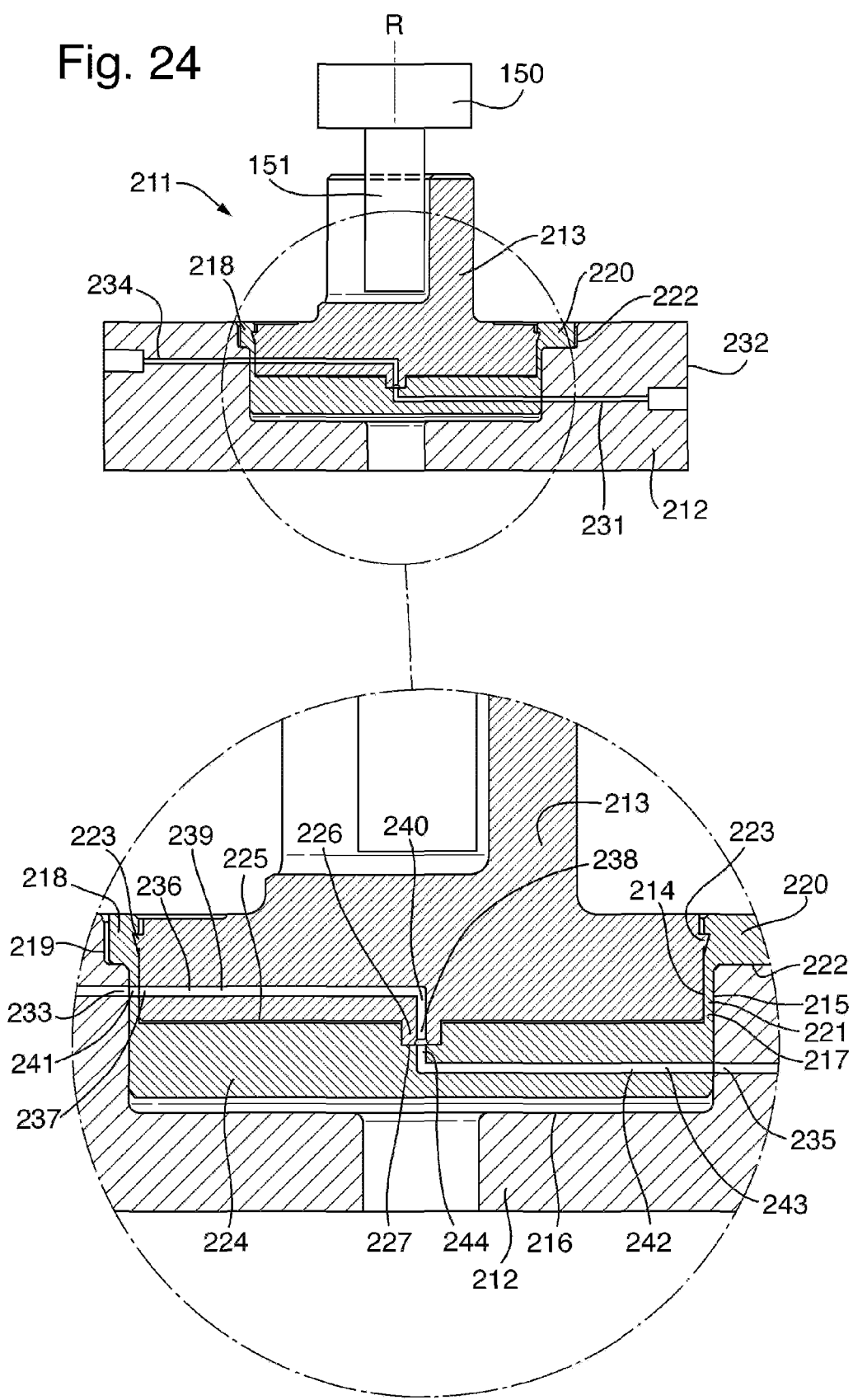
FIG. 24 is a cross-sectional view through the valve assembly of FIG. 22 taken along line XXIV-XXIV.

In the second possible construction in accordance with the second and third aspects of the invention, the valve 110 is formed in a valve assembly 211 illustrated in FIGS. 22 to 24 that is incorporated into the body 37 of the cartridge 10.

The valve 110 comprises a stator 212 and a rotor 213, the stator 212 being mounted into the body 37 that may have a construction comprising plural plates fixed together with channels defined therebetween, similar to the construction of the body 120 in the first possible construction of the valve 110 described above.

The rotor 213 has an outer, annular surface 214 and is mounted on the stator 212 in a recess 216 in the stator 212 having an inner, annular surface 215 that faces the annular surface 214 of the rotor 213. The rotor 213 is mounted inside a liner 215 also arranged inside the recess 214 between the annular surface 214 of the rotor 213 and the annular surface 215 of the stator 212.

The liner 217 comprises an annular wall 221 disposed between the annular surface 214 of the rotor 213 and the annular surface 215 of the stator 212. The annular wall 221 has a rim 218 that protrudes outwardly and sits in a widened opening 219 of the recess 214. The rim 218 has a radial protrusion 220 fitting in a notch 222 in the widened opening 219 that prevents rotation of the liner 217 relative to the stator 212, and the liner 217 is fixed to the stator 212 for example by adhesive. Thus the liner 217 has a fixed position relative to the stator 212.

The liner has a base 224 covering an end surface 225 of the rotor 213 that extends transversely to the rotational axis R. The rotor 213 has a boss 226 formed on its end surface 225 and protruding into a recess 227 formed in the base 224 of the liner 217.

The rotor 213 is capable of rotation about a rotational axis R relative to the liner 217 and hence also relative the stator 212. The annular surface 214 of the rotor 213 and the annular surface 215 of the stator 212 are both parallel to the rotational axis R, although either or both of annular surface 214 of the rotor 213 and the annular surface 215 of the stator 212 could alternatively extend at an acute angle to the rotational axis R. The rotor 213 also has an annular lip 223 protruding from the annular surface 214 that engages the liner 217 and retains the rotor 213 in the liner 217 along the rotational axis R.

The stator 212 defines a plurality of inlet ports 233 in the annular surface 214 of the stator 212 around the rotational axis R. In this example the valve 110 has 96 inlet ports 233 but in general the valve 110 may have any number of ports 233. The inlet ports 233 are evenly spaced, except for a gap at one position. The size of the valve 110 is minimised by arranging the inlet ports 233 as close together as possible, but the same operation could be achieved by increasing the size of the gap in the inlet ports 233 so that the inlet ports 233 extend around a smaller part of the annulus. The inlet ports 233 are formed in the end of channels 234 that extend through the stator 212 to the outer surface 232 of the stator 212 where the channels 234 communicate with channels formed in the body 37 that connect the wells 102 of the well plate 100 to respective inlet ports 233.The channels formed in the body 37 provide this connection to the wells 102 through an array of nozzles 140 arranged as shown in FIG. 19 and described above.

The stator 212 further defines an outlet port 235 in the annular surface 214 of the stator 212 separated from the inlet ports 233 along the rotational axis R, level with the base 224 of the liner 217. The outlet port 135 is formed in the end of a channel 231 that extends through the stator 212 to the outer surface 232 of the stator 212 where the channel 231 communicates with a channel formed in the body 37.

The rotor 213 defines a passage 236 that extends from a first port 237 to a second port 238. The first port 237 is formed in the annular surface 214 of the rotor 213 and is axially aligned with the inlet ports 233 of the stator 212. The second port 238 is positioned on the rotational axis R, being formed in particular in the boss 226. The passage 236 has a radial portion 239 extending from the first port 237 to the rotational axis R and an axial portion 240 extending along the rotational axis R to the second port 238.

The liner 217 provides communication between the inlet ports 233 of the stator 212 and the first port 237 of the rotor 213, as follows. The liner 217 has a plurality of inlet channels 241 that extending through the annular wall 221 between the annular surface 214 of the rotor 213 and the annular surface 215 of the stator 212. Each inlet channel 241 is aligned with, and communicates with, an inlet port 233 of the stator 212. Thus, the inlet ports 233 are evenly spaced, except for a gap at one position. Depending on the rotational position of the rotor 213, the first port 237 of the rotor 213 may be aligned with, and communicate with, any one of the inlet channels 241, or may be aligned with the gap to close the valve 110.

The liner 217 also provides communication between the second port 238 of the rotor 213 and the outlet ports 235 of the stator 212, as follows. The liner 217 defines a passage 242 in its base 224 that extends from the second port 238 of the rotor 213 to the outlet port 235 of the stator 212. The passage 242 has an axial portion 244 extending along the rotational axis R from the second port 238 in the recess 227 and a radial portion 243 extending to the outlet port 238. As a result, the passage 236 in the rotor 213 is in communication with outlet port 235 of the stator 212 through the passage 242 in the liner 217.

Thus, the valve 110 is capable of providing communication between any one of the inlet ports 233 and the outlet port 236 depending on the rotational position of the rotor 113. Rotation of the rotor 213 allows individual inlet ports 233 to be selectively connected. When the first port 237 of the rotor 213 is aligned with the gap in the inlet ports 233 and the gap in channels 241, the passage 236 is closed against the annular wall 217 of the liner 215, thereby closing the valve 110. However, as an alternative, the inlet ports 233 can be brought together to omit the gap so that inlet ports are arranged in a complete annulus and the valve 110 cannot be closed.

As compared to the first construction of the valve 110, the arrangement of the inlet ports 233 of the stator 213 in the annular surface 215 that extends around the rotational axis R, facing the rotational axis R, simplifies the overall construction with the inclusion of relatively high numbers of inlet ports 233. This is achieved whilst still providing adequate sealing around the inlet ports 233 and the first port 237 by means of the liner 217 sealing between the annular surface 214 of the rotor 213 and the annular surface 215 of the stator 212. The stator 212 and the rotor 213 may be made from materials having suitable mechanical properties, whilst making the liner 217 of a material selected to have a greater compliance than the stator 212 and the rotor 213, to provide the required degree of sealing between the annular surface 214 of the rotor 213 and the annular surface 215 of the stator 212. Sealing between the passage 236 and the passage 242 is provided between the boss 226 and recess 227, on either or both of the radial or axial surfaces thereof. In contrast, if the liner 217 was absent, then it would be difficult to select materials for the stator 212 and the rotor 213 provide the required mechanical properties and the required sealing between the annular surface 214 of the rotor 213 and the annular surface 215 of the stator 212, in particular when providing a large number of ports and handling small volumes.

The rotor 213 may be formed from a variety of materials that provide sufficient rigidity, and preferably selected to provide a low coefficient of friction against the liner 217. By way of example, the rotor 213 may be made from any one of ultra-high-molecular-weight polyethylene (UHMWPE), polytetrafluoroethylene (PTFE), perfluoroalkoxy (PFA) or fluorinated ethylene propylene (FEP) (or indeed from any combination of such materials).

The stator 212 may be made from a variety of materials that provide sufficient rigidity. This may be the same material as the rotor 213 or may be a different material, a wider choice of materials being available because there is no need to provide a low coefficient of friction. By way of example, the stator 212 may be made from any one of ultra-high-molecular-weight polyethylene (UHMWPE), polytetrafluoroethylene (PTFE), perfluoroalkoxy (PFA), fluorinated ethylene propylene (FEP), poly(methyl methacrylate) (PMMA) or cyclic olefin co-polymer (COC) (or indeed from any combination of such materials).

The liner 217 may be made from a variety of materials that have a greater compliance than the stator 212 and the rotor 213, and preferably selected to provide a low coefficient of friction against the rotor 213. By way of example, the liner 217 may be made from any one of polytetrafluoroethylene (PTFE), perfluoroalkoxy (PFA), fluorinated ethylene propylene (FEP) or combination of PTFE and an elastomer (e.g. silicone) (or indeed from any combination of such materials).

In this example, the liner 217 has a fixed position relative to the stator 213, but as an alternative the liner 217 could have a fixed position relative to the rotor 212, in which case only a single channel 214 would be required.

The valve 110 having the second possible construction is connected to other components of the fluidics system 31 and the cartridge 10, and is operated, in the same manner as described above for the first possible construction for the valve 110. The valve 110 in its first or second possible construction is not limited to use in the cartridge 10 and can be used in other applications. The valve 110 may be used for flow in the opposite direction to the inlet ports 133 or 233 from outlet port 135 or 235 so more generally the inlet ports 133 or 233 may be referred to as first ports and the outlet port 135 or 235 may be referred to as a second port. The valve 110 is particularly suited as a miniature element for handling low volumes of fluid, in which the fluidics channels, (for example the inlet ports 133, the passage 136, the collection chamber 134 and the outlet port 135 in the first possible construction or the inlet ports 233, the passage 236, the passage 242 and the outlet port 235 in the second possible construction) have cross-sectional areas of no more than 10 mm$^2$, preferably no more than 1 mm$^2$.

Figure 21:
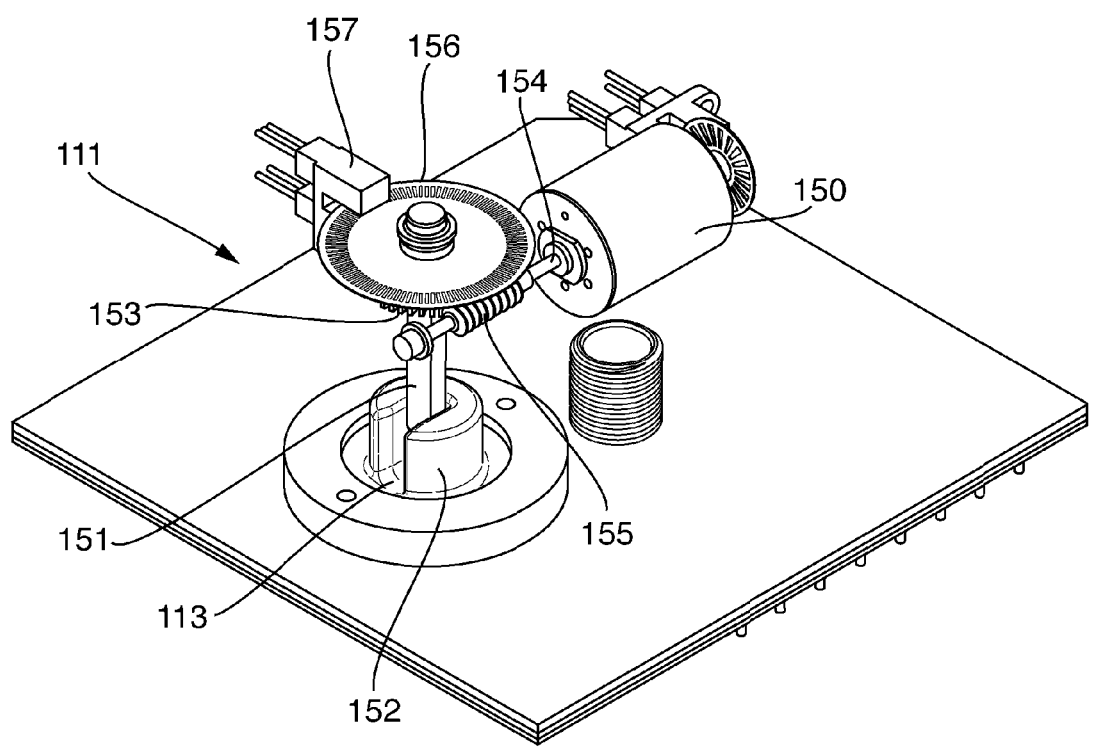
FIG. 21 is a perspective view of the valve assembly including a motor.

The rotor 113 or 213 is actuated by a motor 150, as shown in FIGS. 21 and 24. As shown in FIG. 21, the rotor 113 has a coupling element 152 protruding upwardly from the rotor 113 and into which is fitted a drive shaft 151 that mounts a gear wheel 153. The motor 151 has an output shaft 154 that mounts a gear profile 155 engaging the gear wheel 153 so that the motor 150 drives rotation of the drive shaft 151 and hence the rotor 113 or 213. The drive shaft 151 also mounts an encoder wheel 156 whose position is sensed by a sensor 157. The motor 150 is driven based on the output of the sensor 157, allowing the rotor 113 to be rotated around to select the desired inlet port 133.

The fluidics system 31 is controlled to perform the biochemical analysis in respect of successive samples sequentially. The sensor device 14 is prepared and then the fluidics system 31 is controlled to supply the sample from one of the wells 102 to the sensor device 14. After the biochemical analysis has been performed, the sensor device 14 is emptied and flushed to clear the sample. Then the sensor device 14 is prepared again and the fluidics system 31 is controlled to supply the sample from the next well 102 by rotating the rotor 112 or 212 of the valve 110. A specific example of the method of using the cartridge 10. The materials used are those described in detail in WO-2009/077734.

First, a pre-treatment coating is applied to modify the surface of the body 20 of the sensor device 14 surrounding the wells 21 to increase its affinity to the amphiphilic molecules. The required volume pre-treatment is a hydrophobic fluid, typically an organic substance, in an organic solvent is drawn from a reservoir 30 and dispensed by an inlet pump 33 by means of the supply channels 32 to fill the chamber 24 covering the body 20 and the wells 21. The excess material is expelled into the waste reservoir 35.

The cartridge 10 may be used in various configurations to expel the excess pre-treatment. One example is to apply a gas flow with an inlet pump 33 through the supply channels 32 and chamber 24 to move the fluid through the outlet channel 36 into the waste reservoir 35. Alternatively, the pre-treatment may be dispensed from the inlet pump 33 with gas behind the required volume and the excess expelled through the chamber 24 into the outlet channel 36 into the waste reservoir 35 in a single action. The gas flow is continued through the chamber 24 to flush solvent vapour from the system until the final pre-treatment coating is achieved. In further modification, this final step may be achieved more rapidly by warming the gas flow or the body 20.

After application of the pre-treatment coating an aqueous solution, containing amphiphilic molecules, is flowed across the body 20 to cover the wells 21. The required volume of aqueous solution is drawn from the appropriate reservoir 30 and dispensed by an inlet pump 33 by means of the supply channels 32 to fill the chamber 24 covering the body 20 and the wells 21.

Formation of the amphiphilic membrane 26 is formed with the amphiphilic molecules either directly or improved if a multi-pass technique is applied in which aqueous solution covers and uncovers the recess wells 21 at least once before covering the wells 21 for a final time. The aqueous solution containing amphiphilic molecules may be drawn directly from a reservoir 30 or in the alternative approach mentioned above formed by passing aqueous solution through the lipid assembly in the flow path of the supply channel 32 to the chamber 24.

In a first example, multiple passes of the solution air interface can be achieve by reversal of the flow in the chamber 24. The flow to and from the reservoirs 30 is prevented by operation of the selector valve 45 and operation of the output pump 34 drawing the amphiphilic molecule containing solution through the supply channels 32 from the chamber 24 and pulling air from the outlet channel 36 to the waste reservoir 35. The direction of the outlet pump 34 is reversed and solution returned across the solution filled wells 21.

The formation of the amphiphilic membrane 26 may be observed by monitoring of the resultant electrical signals across the electrodes 22 and 25 when a potential is applied the formation introducing a resistive barrier and a decreases in the measured current. In the event that an amphiphilic membrane 26 fails to form, it is a simple matter to perform another pass of the aqueous solution air interface.

Alternatively, in a second example, multiple passes of solution air interface can be achieved by flow in a single direction by inclusion of air slugs in the solution supply. In this second example, the aqueous solution containing amphiphilic molecules is drawn into an inlet pump 33 from the reservoir 30 and then with operation of non-return valves pumped into the supply channels 32. An air slug may be formed by stopping the amphiphilic molecule aqueous solution flow altering the position of the selector valve 45 and required air volume into the channel behind the solution from the waste reservoir 35 (as it is open to atmosphere) by action of another inlet pump 33. The selector valve 45 is returned to the previous position and further amphiphilic molecule aqueous solution pumped forward. As the inlet pump 33 moves the solution forward through the supply channels 32 to the chamber 24 and through into the outlet channel 36 into the waste reservoir 35, the aqueous amphiphilic molecule solution stream including slugs of air are passed over the wells 21. The process is repeated to achieve the desired number of passes.

Excess amphiphilic molecules are removed from the chamber 24 by flushing aqueous buffer solution from a reservoir 30 by action of an inlet pump 33. Multiple volumes of aqueous buffer solution passed through the chamber 24 into the outlet channel 36 for supply to the waste reservoir 35.

Preparation of the sensor device 14 is completed by flow of aqueous solution containing a membrane protein, for example alpha-hemolysin or a variant thereof, from a reservoir 30 by action of an inlet pump 33 into the chamber over the layer 26 allowing the membrane protein is inserted spontaneously into the layer 26 of amphiphilic molecules after a period of time.

In an alternative approach, the membrane proteins may be stored dried. In this case, the aqueous solution may be directed into a second reservoir 30 containing the membrane protein in dried form from an appropriate reservoir 30 by an inlet pump 33 via the supply channels 32 by altering the position of the selector valve 45 used to rehydrate the membrane proteins before using an inlet pump 33 to flow the resulting solution into the chamber 24 over the layer 26.

The insertion process into the layer 26 may be observed by monitoring of the resultant electrical signals across the electrodes 22 and 25 when a potential is applied insertion resulting in an increase in ionic conduction and an increases in the measured current.

When the insertion period is complete removed from the supply channels 32 and chamber 24 by flush of aqueous buffer solution from a reservoir 30 by action of an inlet pump 33. Multiple volumes of aqueous buffer solution passed through the chamber 24 into the outlet channel 36 for supply to the waste reservoir 35.

Analysis of the samples contained in the well plate 100 may start on completion of preparation of the sensor device 14. The rotary valve 110 is configured to allow fluid contact with the first inlet port 133. The selector valve 45 is positioned to stop flow from the fluid reservoirs 30 and the outlet pump 34 operated to draw the sample material from the sample well 102. The rotary valve 110 is repositioned to direct flow towards the supply channels 32 and fill the chamber 24 to cover the membrane layers 26 of the sensor system. On completion of the analysis the selector valve 45 is positioned to allow flow of aqueous buffer from the inlet pump 33 to flush the sample from the supply channels 32, the rotary valve 110 and the chamber 24 with multiple volumes of buffer through the outlet channel 36 into the waste reservoir 35 to prevent contamination of succeeding samples.

The selector valve 45 is positioned to stop flow from the fluid reservoirs 30 and valve 110 is re-positioned to form fluid connection to the next sample well 102 in the well plate 100. This process repeated for all samples.

After all the samples have been analysed, either the cartridge 10 may be disposed of. Alternatively, as the well plate 100 is a separate element, it may be removed, disposed of and replaced by a new well plate 100 loaded with fresh samples. Such use of the well plate 100 as a disposable element allows re-use of the cartridge 10.

The sensor device 14 is formed in a chip that is mounted on a printed circuit board (PCB) 38 electrically connected to the PCB 38. Electrical contacts from the PCB 38 are arranged as an edge connector pad for making electrical connection to the sensor device 14. On insertion of the cartridge 10 into the module 2, the contacts 39 make electrical connection to the remainder of the electrical circuit in the module 2 that is described below. Three alternative designs for the sensor device 14 and PCB 38 are as follows.

Figure 5:
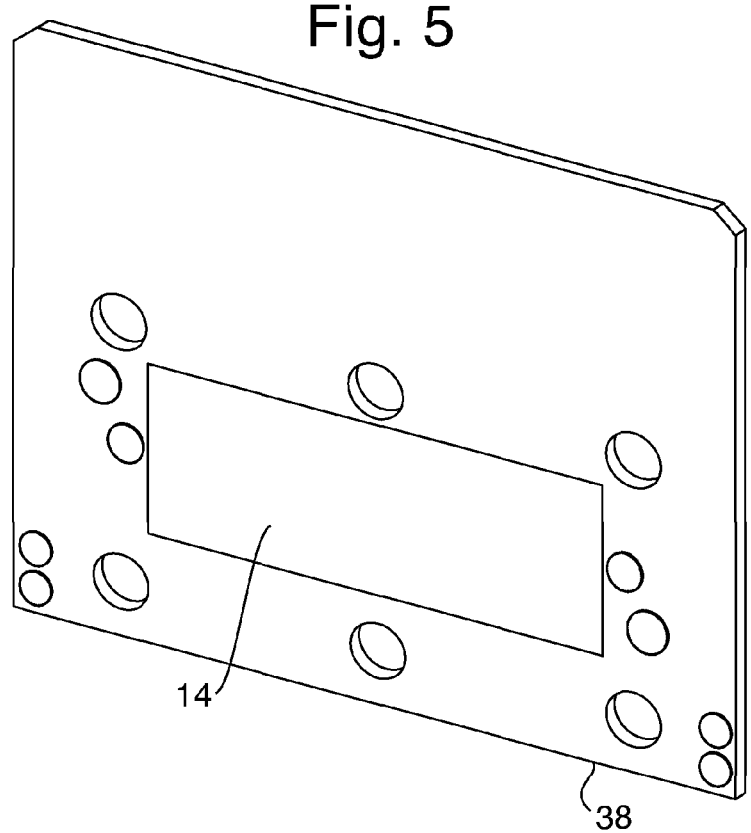
FIGS. 5 and 6 are top and bottom perspective views of the sensor device mounted on a PCB.
Figure 6:
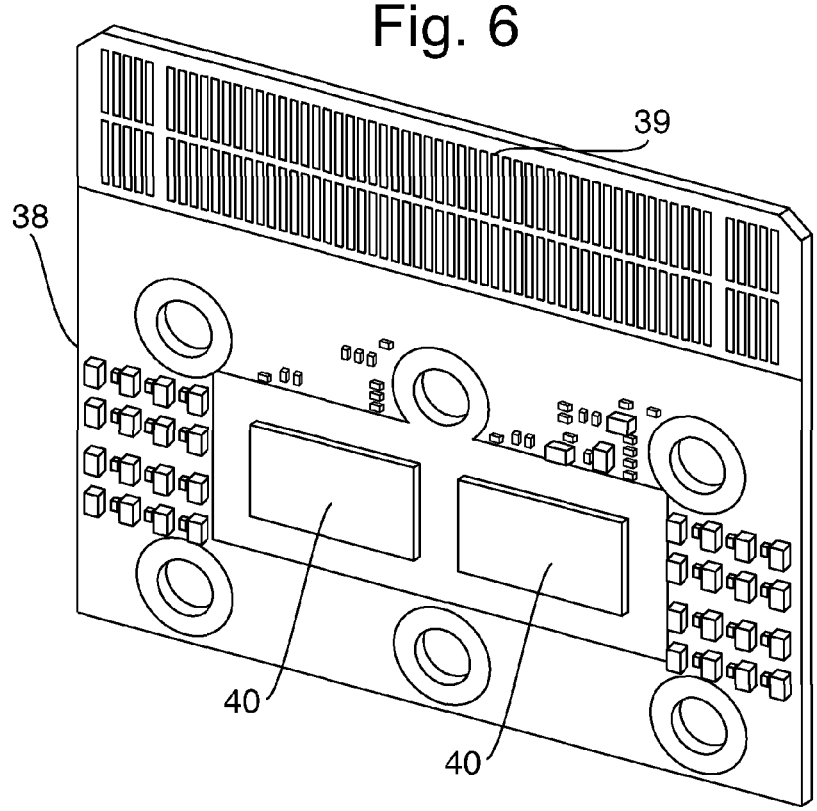

In the first possible design shown in FIGS. 5 and 6, the sensor device 14 is formed as disclosed in WO-2009/077734 as an array of electrodes embedded in wells fabricated on silicon with wells made in a suitable passivation layer on top of the silicon, with the electrical connections at the base of the silicon substrate using through wafer vias, solder-bump bonded to the PCB 38. The PCB provides has an equivalent number of connections to two (or in general any number of) application specific integrated circuits (ASICs) 40 bonded in similar fashion to the opposite side of the PCB 38. The ASICs 40 include some of the components of the electrical circuit of the module 2 described below. The ASICs 40 may include components of the processing circuit for processing the electrical signals from the sensor device 14, for example an amplifier, a sampling circuit and an analog-to-digital converter (ADC) to provide a digital output. The digital output is supplied from the contracts 39 to enable the digital output to leave the sensor device 14 using a suitable interface, for example low-voltage differential signalling (LVDS). Alternatively, the output signal may be provided in amplified analog form with ADC provided within the module. The ASICs 40 may also include some components of control circuits for example accepting power and control commands via the contacts in order to set and monitor functioning parameters, including for example current measurement sample rate (1 Hz to 100 kHz), integration capacitors, bit resolution, applied bias voltage.

The second possible design is to form the sensor device 14 as a simple electrode array chip fabricated on silicon, mounted on the PCB 38 and wire-bonded to the contacts 39. This connection can then interface into the electrical circuit, either as a series of discrete channels, or using an appropriate ASIC. Such an ASIC may be a conventional electronic readout chip, for example as supplied by FLIR Systems, (e.g. FLIR ISC 9717) as an arrayed electrode measurement device.

The third possible design is to fabricate the sensor device 14 and ASIC 40 as one device that is then mounted on the PCB 38.

Figure 7:
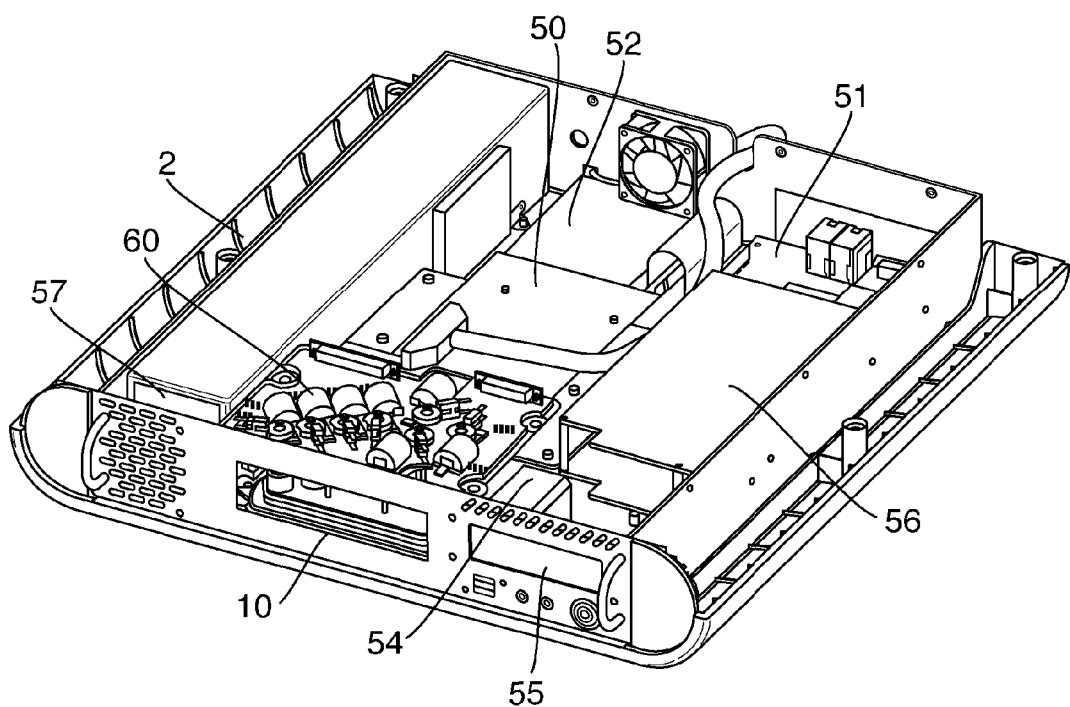
FIG. 7 is a perspective view of the module.

The configuration of the module 2 will now be described with reference to FIG. 7 which shows the module 2 with the housing 11 removed to show the physical layout. The module 2 includes an internal board 50 and an embedded computer 51 connected together by a PCI data acquisition module 52, which together provide an electrical circuit described below. The internal board 50 makes contact with the contacts 39 of the cartridge 10 on insertion into the module 2.

The embedded computer 51 may be a conventional computer, including a processing unit and a storage unit. The embedded computer 51 includes a network interface 53 that allows the module 2 to connect to the network 3, thereby turning the module 2 into a standalone network device yet also providing 'hooks' to enable many modules 2 to be run, managed and controlled as a cluster, as described below. For example, the embedded computer 51 may run a slimmed down operating system (e.g. LINUX) and applications to perform the various functions described below. Complete development kits for such embedded systems are commercially available.

The module 2 includes a loading mechanism 54 for automatically loading and ejecting the cartridge 10 to and from the module 2. The loading mechanism 54 may be for example a proprietary mechanism driven by a high precision stepper motors.

The module 2 also includes a microcontroller 58 and an FPGA 72 mounted on the internal board 50 that control various components of the module 2 as described below.

The module 2 also includes fluidics actuation unit 60 that is mounted on the internal board 50 and controls the fluidics system 31.

The module 2 also comprises a thermal control element 42 arranged to control the temperature of cartridge 10 and the sensor device 14 in particular. The thermal control element 42 may be for example a Peltier thermal controller, such as a 32 watt Single Stage Thermoelectric Module (for example as supplied by Ferrotec Corp, 33 Constitution Drive, Bedford N.H. 03110 USA—part number 9500/071/060B). The thermal control element 42 may be mounted, for example, underneath the cartridge 10 and so is not visible in FIG. 7. The thermal control element 42 may be considered as part of the analysis apparatus formed primarily by the cartridge 10 and could alternatively be mounted on the cartridge 10.

Lastly, the module 2 includes a display 55 for displaying basic operational status information, a power supply 56 for supplying power to the various components of the module 2, and a cooler assembly 57 for cooling the module 2.

Figure 8:
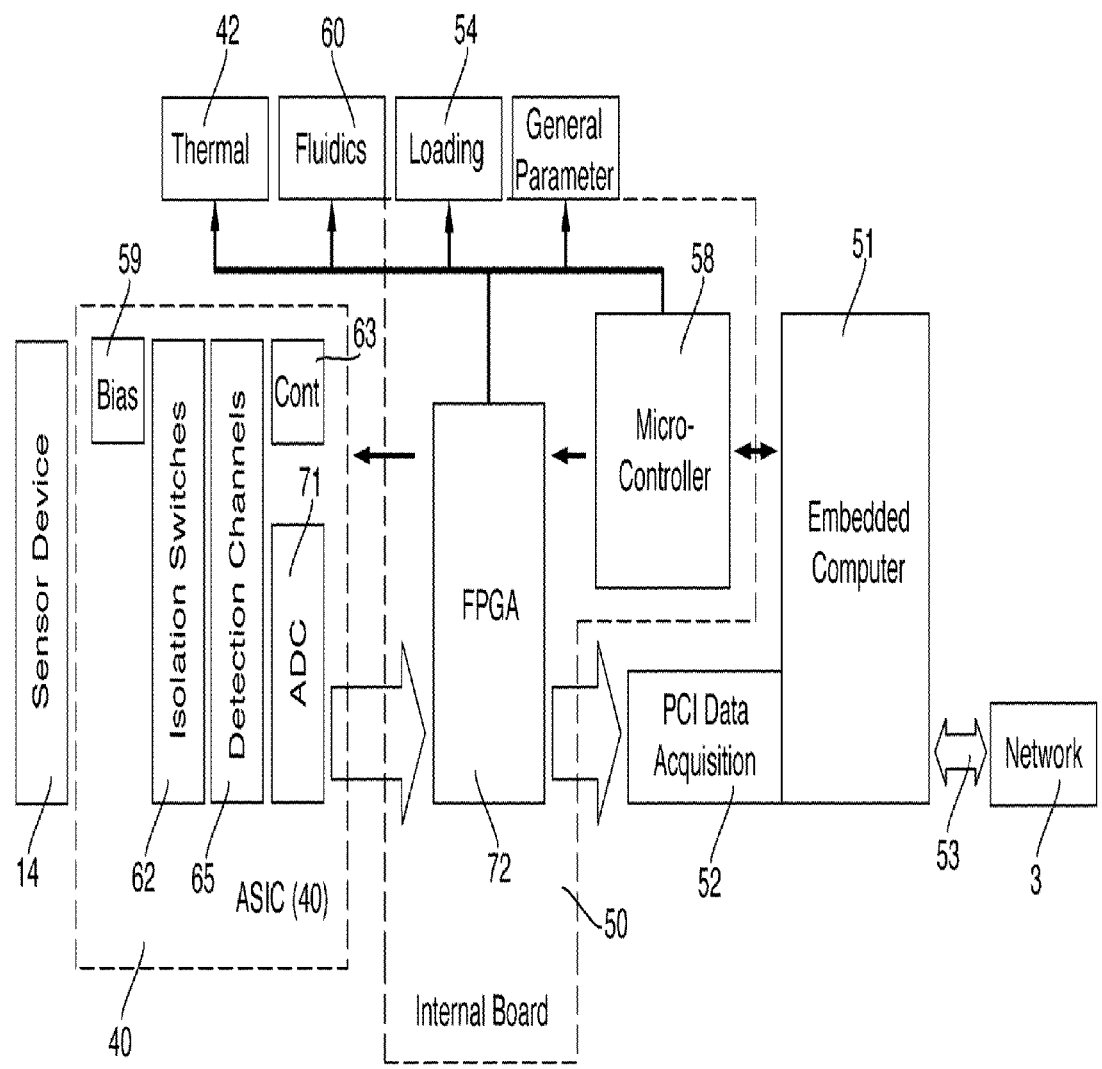
FIG. 8 is a schematic diagram of the electrical circuit of a module.
Figure 9:
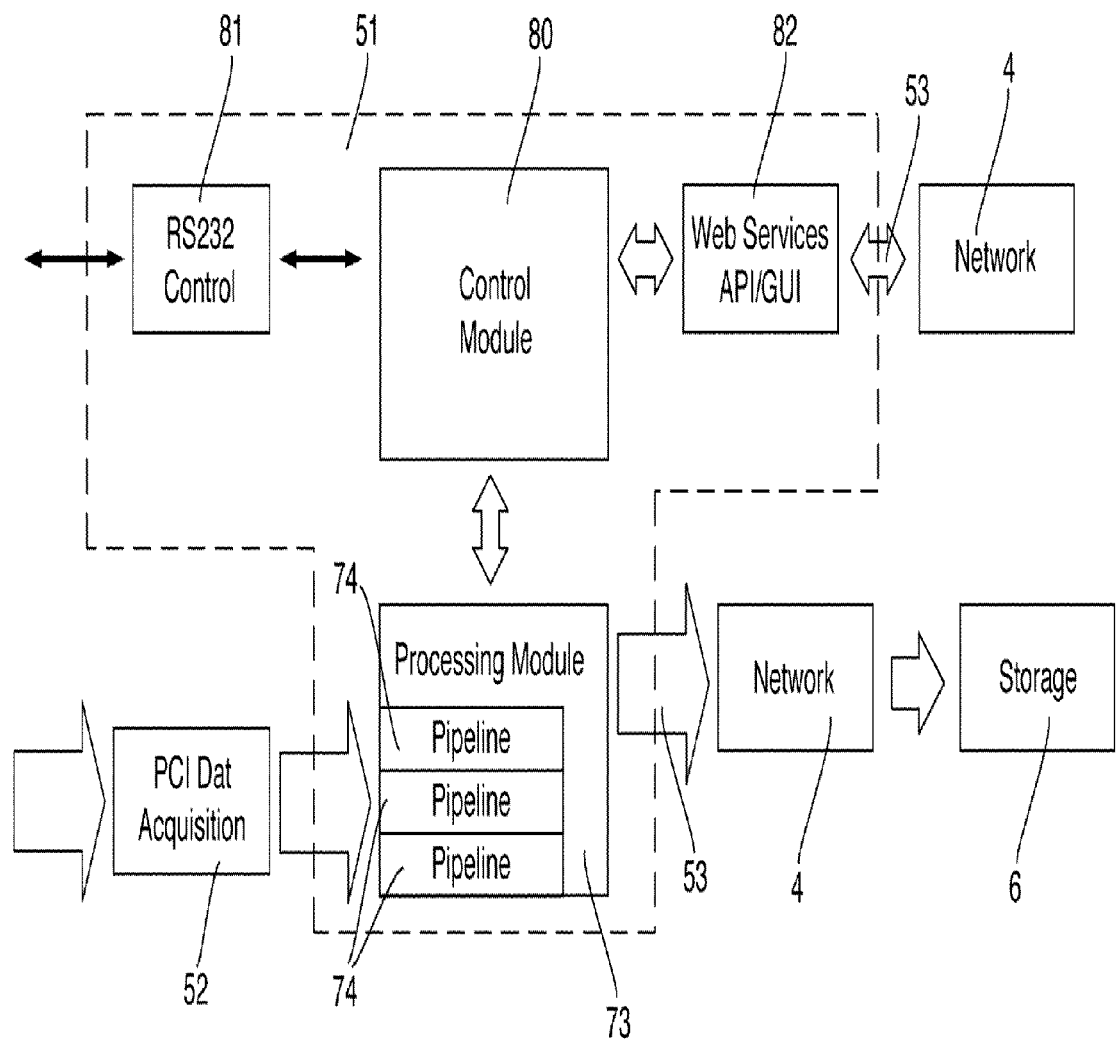
FIG. 9 is a schematic diagram of the control unit.

The electrical circuit provided by the internal board 50 and the embedded computer 51 will now be described with reference to FIGS. 8 and 9. The electrical circuit has two main functions, namely a signal processing function and a control function, so that it acts as both a signal processing circuit and as a control unit for the module 2.

The signal processing function is distributed between the internal board 50 and embedded computer 51 and is provided as follows.

The sensor device 14 is connected to a switch arrangement 62 formed in an ASIC 40 on the PCB 38 of the cartridge 10 and controlled by the control interface to the ASIC 40. The switch arrangement 62 is arranged to selectively connect the well electrodes 22 of the sensor device 14 to a respective contact for supply to a detection channel of the signal processing function, there being a greater number of wells 21 than detection channels. The switch arrangement 62 is arranged and operated as described in detail in U.S. Application No. 61/170,729 which is incorporated herein by reference.

Alternatively the switch arrangement 62 may be provided and controlled separately from the ASIC 40 as a standalone functional block between the sensor device 14 and the detection channels 65, the detection channels 65 being provided within a readout chip, for example as supplied by FLIR Systems, (e.g. FLIR ISC 9717).

Figure 10:
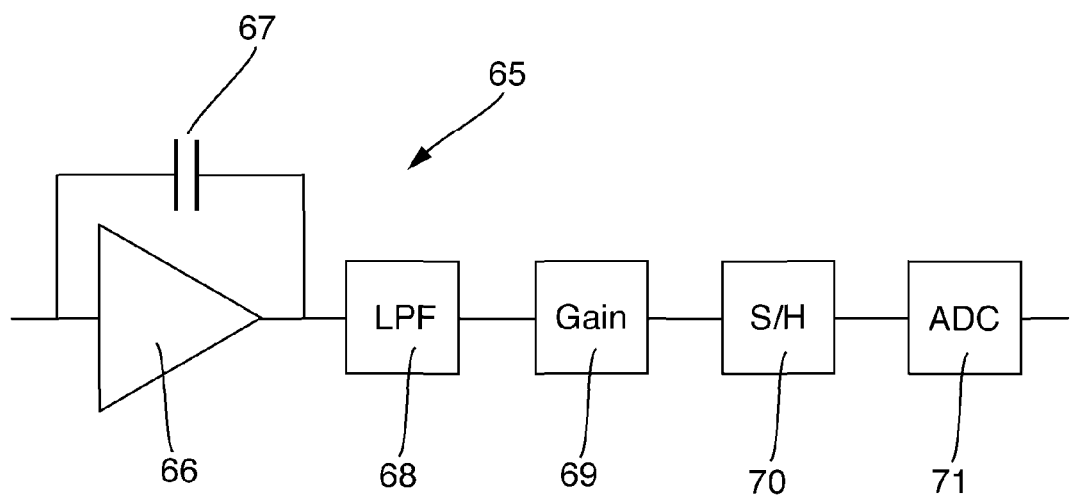
FIG. 10 is a diagram of a detection channel.

The ASIC 40 provides an array of detection channels 65 each arranged as shown in FIG. 10 to amplify the electrical signal from one of the well electrodes 26. The detection channel 65 is therefore designed to amplify very small currents with sufficient resolution to detect the characteristic changes caused by the interaction of interest. The detection channel 65 is also designed with a sufficiently high bandwidth to provide the time resolution needed to detect each such interaction. These constraints require sensitive and therefore expensive components.

The detection channel 65 includes a charge amplifier 66 that is arranged as an integrating amplifier by means of a capacitor 67 being connected between an inverting input of the charge amplifier 66 and the output of the charge amplifier 66. The charge amplifier 66 integrates the current supplied thereto from the well 21 to provide an output representative of the charge supplied in successive integration periods. As the integration periods are of fixed duration the output signal is representative of current, that duration being short enough to provide sufficient resolution for monitoring of events occurring in the well 21 connected thereto. The output of the charge amplifier 66 is supplied through a low pass filter 68 and a programmable gain stage 69 to a sample-hold stage 70 that is operated to sample the output signal from the charge amplifier 66 and produce a sampled current signal. The output current signal is supplied to an ADC 71 to convert it into a digital signal. The digital signals from each detection channel 65 are output from the ASIC 40.

The digital signals output from the ASIC 40 are supplied via the contacts 39 from the PCB 38 of the cartridge 10 to a field programmable gate array (FPGA) 72 provided on the internal board 50 of the module 2. The FPGA 72 includes a buffer arranged to buffer the digital signals from each detection channel 65 before supply via the PCI data acquisition module 52 to the embedded computer 51.

In an alternative arrangement, the digital output from the detection are provided from a readout chip located on the internal board 50 of the module 2 and supplied to the FPGA 72.

The embedded computer 51 is arranged as follows to process the digital current signals from each detection channel 65 as follows. A PCI data acquisition module 52 controls the transfer of the digital current signals from the FPGA 72 to the embedded computer 51 where it is stored as digital data.

Thus the digital data stored in the embedded computer 51 is raw output data representing the current measured by each well electrode 22 in respect of a nanopore in the amphiphilic membranes 26 of the corresponding well. The current from each nanopore is a channel of the measured electrical signal. This raw data is processed by a processing module 73 that includes a pipeline 74 in respect of each channel. The processing module 73 is implemented by software executed in the embedded computer 51.

The nature of the signal processing performed in each pipeline 74 of the processing module 73 is as follows. The pipeline 74 processes the raw data to produce output data representing the results of the biochemical analysis in respect of the corresponding channel. As discussed above, interactions between the nanopore and the sample cause characteristic changes in the electrical current that are recognisable events. For example, an analyte passing through the nanopore may cause the electrical current to reduce by a characteristic amount. Thus, the pipeline 74 detects those events and generates output data representing those events. Examples of such processing are disclosed in WO2008/102120 which is incorporated herein by reference. The output data may simply represent the fact that the event has occurred.

Additionally, the pipeline may classify the event and the output data may represent the classification of the event. For example, the nanopore may have an interaction that differs as between different analytes in the sample causing a different modulation of the electrical signal. In this case, the pipeline 74 classifies the analyte on the basis of the modulated electrical signal. An example of this is that a nanopore may have an interaction with bases of a polynucleotide in which each base modulates the electrical signal differently. For example, a base passing through the nanopore may cause the electrical current to reduce by an amount that is characteristic of the base. In this case, the pipeline 74 classifies the event by identifying the base from the modulation of the electrical signal. In this manner, the biochemical analysis is sequencing of a polynucleotide in the sample, and the output data includes sequence data representing a sequence of the polynucleotide. This may be referred to as "base calling".

The pipeline 74 also produces output data that is quality data representative of the quality of the output data that represents the results of the biochemical analysis. This may represent a probability of the detection and/or classification of the events being incorrect.

The output data may be represented in any suitable format. In the case of sequencing of a polynucleotide, the output data and the quality data may be represented in the FASTQ format which is a conventional text-based format for a nucleotide sequence and its associated quality scores. The output data is stored in the embedded computer 51 and may also be transferred over the network 3 and stored on the storage device 6. The raw data representing the electrical signals across each nanopore may be stored as well as the final output data, depending on user requirements.

The processing module 73 may also derive and store quality control metrics representing parameters of the biochemical analysis itself.

Aspects of the signal processing performed by the pipeline 74 may be performed on the internal board 50 before data is transferred to the embedded computer 51. This approach is of particular use for large numbers channels and the FPGA 72 may be particularly suited to this type of task.

There will now be described the control function that is arranged to control the operation of the module 2. The control function is distributed between the internal board 50 and embedded computer 51 and is provided as follows.

The control function includes a controller 58, for example a Cortex M3 Microcontroller, provided on the internal board 50. The controller 58 controls the operation of all the components of the analysis apparatus 13. The controller 58 is arranged to send, via standard protocols and through low level device drivers, commands to the pumps 33 and 34 of the fluidics system 31 and other pre-requisites for reading data. Status information is stored based on error codes derived from drivers.

The controller 58 is itself controlled by a control module 80 that is implemented in the embedded computer 51 by software executed thereon. The control module 80 communicates with the controller 58 via an RS232 interface 81. The control module 80 controls the controller 58 as follows so that they operate together to constitute a control unit for the module 2.

The controller 58 controls the loading mechanism 54 to load and eject the cartridge 10. On loading the controller 58 detects that proper electrical contact is made between the contacts 39 and the internal board 50.

The controller 58 controls the fluidics actuation unit 60 to control the fluidics system 31 to prepare the sensor device 14.

During this preparation, the control module 80 may monitor the electrical signals output from the sensor device 14 to detect that preparation occurs correctly, for example using the analysis techniques disclosed in WO-2008/102120 which is incorporated herein by reference. Typically, the control module 80 will determine which of the wells 22 are set-up correctly at the start of a run. This may include sensing bi-layer quality, electrode quality, occupancy by a pore and even whether the nanopore is active following the sensing of a sample.

On the basis of this monitoring, the controller 58 also controls the switching controller 63 to cause the switch arrangement 62 connect detection channels 65 to the well electrodes 26 of wells 22 of the sensor device 14 that have acceptable performance, in the manner disclosed in detail in U.S. Application No. 61/170,729.

In the case of sequencing of polynucleotides, the control module 80 may also sense the presence and state of any modifications to nanopores that might be required in order to process and measure DNA, e.g. attachment of exonuclease enzymes, cyclodextrin adaptors.

The controller 58 controls a bias voltage source 59 that supplies a bias voltage to the common electrode 25. In this way, the controller 58 controls the bias voltage across each nanopore. The controller 58 controls the thermal control element 42 to vary the temperature of the analysis apparatus 13. The controller 58 controls the operation of the ASIC 40 to vary the sampling characteristics, for example the sampling rate, the integration period and reset period of the capacitor 67, and the resolution of the resultant signal.

The controller 58 may execute the above control functions and other experimental parameters via the FPGA 72. In particular, control of the ASIC 40 is provided via the FPGA 72.

Once the sensor device 14 has been prepared correctly, then the controller 58 controls the cartridge 10 to introduce the sample into the sensor device 14 and to perform the biochemical analysis. The biochemical analysis is then performed with the result that electrical signals are output from the sensor device 14 and processed by the processing module 73 to produce output data representative of the analysis.

The control module 80 has local performance targets that are derived on the basis of input as discussed below. The local performance targets represent the desired performance for the operation of the module 2. The performance targets can relate to any combination of: the time within which output data is produced; the quantity of output data that is produced; or the quality of output data that is produced, depending on the requirements for the biochemical analysis.

During operation, the control module 80 determines measures of performance of the biochemical analysis, these being of the same nature as the local performance targets, i.e. the time within which output data is produced; the quantity of output data that is produced; or the quality of output data that is produced. On the basis of the measures of performance, the control module 80 controls the controller 58 to control the analysis performed by the module 2 to meet the performance targets. This is done by starting and stopping operation of the analysis apparatus and/or varying the experimental parameters.

In one mode of operation, the plurality of wells 102 may not each contain a different sample 142. That is, a selection of the wells 102 may contain the same sample 142. The information as to which wells 102 contain the same sample 142 could, for example, either be programmed into the analysis apparatus, or could be provided by a default setting in which predetermined wells 102 (for example those on the same row or column) are known to be provided with the same sample 142. In this mode, the control module 80 can be configured to determine whether a performance target has been met after a sample 142 in a well 102 has been used up. In the event the performance target has not been met, the control module 80 can control the analysis to continue using a sample 142 from the selection of wells 102 containing the same sample 142 as that which has been used up. This procedure can be repeated until it is determined that the performance target has been met, at which time the control module 80 can control the apparatus to analyse another sample 142 (of a different type) or bring the analysis to a conclusion.

As a result, there is no need to process repeats of samples 142 for which a successful analysis has been performed, but unexpectedly lengthy analyses can be run until completion. Further, in this mode it may be preferable to supply the samples 142 to the sensor 14 immediately after each other, without an intermediate washing step, especially for example when the samples 142 are the same. In other modes, an intermediate washing step may be desirable between analyzing samples 142, especially for example when the samples 142 are different to each other. However, instead of a washing step, another option is to use a first portion of the next sample 142 to be analysed to displace the previous sample 142, effectively using the sample 142 itself as a washing medium.

This operation of the control module 80 using local performance targets and measures of performance is described in detail in U.S. Patent Application No. 61/265, 488 to which reference is made and which is incorporated herein by reference.

In the manner described above, each module 2 is a standalone device that can perform a biochemical analysis independently of the other modules 2. A cluster of modules 2 are operated as a common instrument 1 to perform a common biochemical analysis. This operation of a cluster of modules 2 as a common instrument 1 and manner in which the modules 2 connect to the network 3 and communicate on a peer-to-peer basis are described in detail in U.S. Patent Application No. 61/265,488 to which reference is made and which is incorporated herein by reference.

More details on the nature of the biochemical analysis that may be performed are as follows. The following paragraphs refer to numerous documents that are all incorporated by reference.

The cartridge 10 described above can perform biochemical analysis using nanopores in the form of protein pores supported in an amphiphilic membrane 26.

The nature of the amphiphilic membrane 26 is as follows. For amphiphilic systems the membrane 26 is typically composed of lipid molecules or their analogues and can be either naturally occurring (e.g. phosphatidylcholine) or synthetic (DPhPC, diphytanoylphosphatidylcholine). Non-natural lipid analogues may also be used such as 1,2-dioleoyl-3-trimethylammonium-propane (DOTAP). Amphiphilic membranes may be comprised of a single species or a mixture of species. Additives such as fatty acids, fatty alcohols, cholesterol (or similar derivatives) may also be used to modulate membrane behaviour. Amphiphilic membranes provide a high resistive barrier to the flow of ions across the membrane. Further details of amphiphilic membranes that are applicable to the present invention are given in WO-2008/102121, WO-2008/102120, and WO-2009/077734.

In the analysis apparatus 13, the amphiphilic membrane 26 is formed across a well 22, but the cartridge 10 can be adapted to support an amphiphilic membrane in other manners including the following. The formation of electrically addressable amphiphilic membranes can be achieved by a number of known techniques. These can be split into membranes or bilayers that are incorporated onto one or more electrodes and those that provide a divider between two or more electrodes. Membranes attached to the electrode may be bilayers or monolayers of amphiphilic species and may use direct current measurements or impedance analysis, examples of which are disclosed in (Kohli et al. Biomacromolecules. 2006; 7(12):3327-35; Andersson et al., Langmuir. 2007; 23(6):2924-7; and WO-1997/020203. Membranes dividing two or more electrodes can be formed in a number of ways including but not limited to: folded (e.g. Montal et al., Proc Natl Acad Sci USA. 1972, 69(12), 3561-3566); tip-dip (e.g. Coronado et al., Biophys. J. 1983, 43, 231-236); droplets (Holden et al., J Am Chem Soc. 2007; 129(27):8650-5; and Heron et al., Mol Biosyst. 2008; 4(12): 1191-208); glass supported (e.g. WO-2008/042018); gel-supported (e.g. WO-2008/102120); gel-encapsulated (e.g. WO 2007/127327); and tethered and porous-supported (e.g. Schmitt et al., Biophys J. 2006; 91(6):2163-71).

The nanopores are formed by protein pores or channels introduced into the amphiphilic membranes 26. The protein pores or channels may be proteins that are either natural or synthetic, examples being disclosed in WO-00/79257; WO-00/78668; U.S. Pat. No. 5,368,712; WO-1997/20203; and Holden et al., Nat Chem Biol.; 2 (6):314-8)]. Natural pores and channels may include structures where the membrane spanning portion of the protein comprises a beta-barrel, such as alpha-hemolysin (e.g. Song et al., Science. 1996; 274(5294):1859-66), OmpG (e.g. Chen et al., Proc Natl Acad Sci USA. 2008; 105(17):6272-7), OmpF (e.g. Schmitt et al., Biophys J. 2006; 91(6):2163-71) or MsPA (e.g. Butler et al., Proc Natl Acad Sci USA. 2008; 105(52): 20647-52). Alternatively, the membrane spanning portion of the protein may consist of an alpha-helix, such as a potassium channel (e.g. Holden et al., Nat Chem Biol.; 2 (6):314-8), (Syeda et al., J Am Chem Soc. 2008; 130(46):15543-8)]. The pore or channel may be a naturally occurring proteins that is modified either chemically or genetically to provide desired nanopore behaviour. An example of a chemically modified protein pore is given in WO-01/59453 and an example of a genetically modified protein pore is given in WO-99/05167. Adapters may also be added to the system to provide greater control and more targeted analyte detection, examples of which are disclosed in U.S. Pat. Nos. 6,426, 231; 6,927,070; and WO2009044170.

The nanopores allow a flow of ions to travel across the amphiphilic membrane 26. The flow of ions is modulated by pore on the basis of an analyte interaction, thus allowing the nanopore to provide a biochemical analysis. There are many examples of such modulation being used to as the basis for biochemical analysis, for example in U.S. Pat. Nos. 6,426, 231; 6,927,070; 6,426,231; 6,927,070; WO-99/05167; WO-03/095669; WO-2007/057668; WO1997020203; Clarke et al. Nat Nanotechnol. 2009; 4(4):265-270; and Stoddart et al., Proc Natl Acad Sci USA. 2009; 106(19): 7702-7707.

The cartridge 10 may use nanopores for sequencing of polynucleotides, including DNA and RNA, and including naturally occurring and synthetic polynucleotides. It may apply a variety of techniques that have been proposed for deriving sequence information in a rapid and cost effective manner, typically utilising measurement of changes in the electrical signal across a single nanopore as a single strand of DNA passes through the nanopore. Such techniques include without limitation: nanopore-assisted sequencing by hydridisation; strand sequencing; and exonuclease-nanopore sequencing (e.g. D. Branton et al, Nature Biotechnology 26(10), p 1-8 (2009)). The technique may involve the polynucleotide passing through the nanopore as an intact polymer (modified or unmodified), or broken into the constituent nucleotide components or bases (for example using the techniques disclosed in: U.S. Pat. No. 5,795,782; EP-1, 956,367; U.S. Pat. Nos. 6,015,714; 7,189,503; 6,627,067; EP-1,192,453; WO-89/03432; U.S. Pat. No. 4,962,037; WO-2007/057668; International Appl. No. PCT/GB09/001690 (corresponding to British Appl. No. 0812693.0 and U.S. Appl. No. 61/078,687); and International Appl. No. PCT/GB09/001679 (corresponding to British Appl. No. 0812697.1 and U.S. Appl. No. 61/078,695).

In general, present invention may be applied to any apparatus providing the measurement of nanopores by providing two electrodes, one either side of an insulating membrane, into which a nanopore is inserted. When immersed in an ionic solution, a biased potential between the electrodes will drive ionic flow through the nanopore that can be measured as current in an external electrical circuit. This current alters as DNA passes through the nanopore, and with sufficient resolution, the constituent bases can be recognised from the changes, for example as disclosed in Clarke et al. Nat Nanotechnol. 2009; 4(4):265-270; International Appl. No. PCT/GB09/001690 (corresponding to British Appl. No. 0812693.0 and U.S. Appl. No. 61/078, 687); and D. Stoddart, PNAS doi 10.1073/pnas. 0901054106, April 2009.

Further, the present invention may be applied to any apparatus in which arrays of nanopores measure the same sample by providing individually addressable electrodes on one side of each nanopore in the array connected to either a common electrode or an equivalent number of addressable electrodes in the sample on the other side. External circuitry can then perform measurements of DNA passing through each and every nanopore in the array without the synchronisation of base addition to each nanopore in the array, i.e. each nanopore is free to process a single DNA strand independently of every other, for example as disclosed in US-2009/0167288; WO-2009/077734; and U.S. Application No. 61/170,729. Having processed one strand, each nanopore is also then free to begin processing a subsequent strand.

One advantage of nanopore-based analysis is that the quality of measurement does not change over time for a fully-functioning nanopore, i.e. the accuracy of base identification is the same at the start of sequencing as at any point in the future, subject to the expect experimental limitations. This enables each sensor to perform, at constant average quality, multiple analyses in a sequential fashion on the same sample or on multiple samples over time.

Besides sequencing of polynucleotides, the nanopores may be applied to a diverse range of other biochemical analysis, including without limitation: diagnostics (e.g. Howorka et al., Nat Biotechnol. 2001; 19(7):636-9); protein detection (e.g. Cheley et al., Chembiochem. 2006; 7(12): 1923-7; and Shim et al., J Phys Chem B. 2008; 112(28): 8354-60); drug molecule analysis (e.g. Kang et al., J Am Chem Soc. 2006; 128(33):10684-5); ion channel screening (e.g. Syeda et al., J Am Chem Soc. 2008 Nov. 19; 130(46): 15543-8), defence (e.g. Wu et al., J Am Chem Soc. 2008; 130(21):6813-9; and Guan et al., Chembiochem. 2005; 6(10):1875-81); and polymers (e.g. Gu et al., Biophys. J. 2000; 79, 1967-1975; Movileanu et al., Biophys. J. 2005; 89, 1030-1045; and Maglia et al., Proc Natl Acad Sci USA. USA 2008; 105, 19720-19725).

The present invention may also be applied to an analysis apparatus in which nanopores are provided in solid state membranes. In this case the nanopore is a physical pore in a membrane formed from a solid material. Such membranes have many advantages over fluid or semi-fluid layers, particularly with respect to stability and size. The original concept was proposed by researchers at the University of Harvard for examining polymers, such as DNA (e.g. WO-00/79257; and WO 00/78668). Since then the work has expanded to include the following techniques that may be applied in the present invention: fabrication methods (e.g. WO-03/003446; U.S. Pat. No. 7,258,838; WO-2005/000732; WO-2004/077503; WO-2005/035437; WO-2005/061373); data acquisition and evaluation (e.g. WO-01/59684; WO-03/000920; WO-2005/017025; and WO-2009/045472), incorporation of nanotubes (e.g. WO-2005/000739; WO-2005/124888; WO-2007/084163); and the addition of molecular motors (e.g. WO-2006/028508); the use of field effect transistors or similar embedded within nanopore structures (e.g. U.S. Pat. Nos. 6,413,792, 7,001, 792); the detection of fluorescent probes interacting with a nanopore or nanochannel (e.g. U.S. Pat. No. 6,355,420; WO-98/35012); and the illumination and detection of fluorescent probes being removed from their target substrates as they translocate a nanopore (e.g. US-2009-0029477). Even the use of mass spectrometry may be employed in the analysis apparatus, for example as a polymer of interest passes through a nanopore or channel and whose monomers are then cleaved and ionised sequentially analysed using mass spectrometry.

The analysis may be a chemical or biological assay, and could be used to carry out biomarker validation studies, clinical tests and high-throughput screening. These tests may involve carrying out chromatography (HPLC (high performance liquid chromatography, TLC (thin layer chromatography), FPLC (fast protein liquid chromatography), flash chromatography, with detection of analyte in the liquid eluent (by absorbance, fluorescence, radiometric methods, light scattering, particle analysis, mass spectrometry), or an immunoassay or using direct mass spectrometry (MALDI (matrix assisted laser desorption ionization), APCI (atmospheric pressure chemical ionization), ESI (electrospray ionization) ionization with Quadrupole (single and multiple), time-of-flight, ion trap detection). Immunoassays include an ELISA (enzyme-linked immunosorbent assay), lateral flow assay, radioimmunoassay, magnetic immunoassay or immunofluorescence assay.

These tests and assays can be used in the context of: identification of foetal abnormalities such as Down's Syndrome, genome-wide association studies, pharmacokinetic and pharmacodynamic investigations on tissues and whole animals, drug testing in sport, testing for micro-organisms in environmental matrices (sewage, polluted water etc.), testing for hormones and growth factors in treated water and so on.

The analysis may be applied to biomarker validation studies. The present invention can allow very high numbers of samples to be analysed quickly and easily. For example, the current process of biomarker discovery is hampered by the validation step, i.e. once a candidate marker has been found, large numbers of samples must be examined in order to statistically confirm its altered levels in the tissues of interest. An assay must therefore be developed for each marker. The system of the present invention has a single readout for all analytes, for example DNA, RNA, protein or small molecule, cutting down on the assay development stages.

The analysis may be applied to clinical tests and ELISA substitute. When a sample is submitted for tests at a hospital or clinic, the testing procedure is very likely to involve either mass spectrometry or ELISA. Both of these can be supplanted by the system of the present invention. Development of suitable tests on the system of the invention will give huge increases in throughput and savings in sample preparation time and handling. This will apply to large proteins such as growth factors, peptides such as insulin, or small molecules such as drugs of abuse or prescription drugs.

The analysis may be applied to high-throughput screening. Any quantitative screen can be carried out on the system of the present invention. Thus, if an assay (for example a protease assay) that gives a peptide or small molecule as a product is currently used in high-throughput screening, the present invention can increase the throughput and cut down on sample handling and preparation time.

The invention claimed is:

1. A rotary valve comprising:
a stator defining a plurality of first ports, and a second port;
a rotor mounted on the stator for rotation about a rotational axis, the valve comprising a passage being in communication with the second port of the stator and extending to a position for communicating with any one of the plurality of first ports of the stator individually, depending upon the rotational position of the rotor,
wherein the rotor is mounted on the stator inside a liner arranged between an annular surface of the stator and an annular surface of the rotor, the liner being made of a material having a greater compliance than both the rotor and the stator, and
the liner having at least one channel extending through the liner between the annular surface of the stator and the annular surface of the rotor and configured to provide communication between a first port of the rotor and any one of the plurality of first ports of the stator, depending on the rotational position of the rotor.

2. A rotary valve according to claim 1, wherein the first ports, the passage, and the second port have cross-sectional areas of no more than $10mm^2$, preferably no more than $1mm^2$.

3. A rotary valve according to claim 1, wherein the plurality of first ports comprises 24 first ports or more.

4. A rotary valve according to claim 1, wherein the liner is fixed relative to the rotor.

5. A rotary valve according to claim 1, wherein:
the plurality of first ports defined by the stator is arranged around the rotational axis, and the rotor defines the first port capable of communication with any one of the first ports of the stator depending on the rotational position of the rotor, a second port positioned on the rotational axis and in communication with the second port of the stator, and the passage extending between the first port and the second port.

6. A rotary valve according to claim 5, wherein the ports of the stator and the rotor, and the passage of the rotor have cross-sectional areas of no more than $10mm^2$, preferably no more than $1mm^2$.

7. A rotary valve according to claim 5, wherein the plurality of first ports of the stator are provided in an annular surface that extends around a rotational axis, facing the rotational axis, and the first port of the rotor is defined in an annular surface of the rotor that faces the annular surface of the stator.

8. A rotary valve according to claim 7, wherein the liner has a base covering an end surface of the rotor that extends transversely to the rotational axis, the base having a passage that extends from the second port of the rotor to the second port of the stator so that the passage in the rotor is in communication with the second port of the stator through the passage in the liner.

9. A rotary valve according to claim 8, wherein the rotor has a boss formed on the end surface of the rotor protruding into a recess in the liner, the second port of the rotor being formed in the boss and the passage extending from the recess, the boss and the recess providing a seal therebetween.

10. A rotary valve according to claim 8, wherein the second port of the stator is defined in the annular surface of the stator.

11. A rotary valve according to claim 7, wherein the passage in the rotor communicates with a passage in the liner that is in communication with the second port of the stator.

12. A rotary valve according to claim 7 wherein the liner has a fixed position relative to the stator, and said at least one channel is a plurality of channels each in communication with one of the plurality of first ports of the stator and capable of communication with the first port of the rotor, depending on the rotational position of the rotor.

13. A rotary valve according to claim 7, wherein the rotor has an annular lip engaging the liner and retaining the rotor in the liner along the rotational axis.

14. A rotary valve according to claim 7, wherein the annular surface of the rotor is parallel to the rotational axis.

15. A rotary valve according to claim 7, wherein the annular surface of the stator is parallel to the rotational axis.

16. A rotary valve according to claim 5, wherein the stator is on a body that is arranged to allow attachment of a well plate comprising a plurality of wells corresponding to the plurality of first ports, the body defining channels connecting the wells to the corresponding first ports.

17. A rotary valve according to claim 1, wherein:
the stator defines the plurality of first ports in the annular surface that extends around the rotational axis, facing the rotational axis;
the rotor is mounted on the stator for rotation about the rotational axis inside a the liner arranged between the annular surface of the stator and the annular surface of the rotor that faces the annular surface of the stator, the liner being made of a material having a greater compliance than both the rotor and the stator,
the rotor comprises the passage, the passage extending from the first port defined in the annular surface of the rotor and being in communication with the second port of the stator, and
the liner has at least one channel extending through the liner between the annular surface of the stator and the annular surface of the rotor and configured to provide communication between the first port of the rotor and any one of the plurality of first ports of the stator, depending on the rotational position of the rotor.

18. A rotary valve according to claim 17, wherein the ports of the stator and the rotor, the passage of the rotor and the at least one channel of the liner have cross-sectional areas of no more than $10mm^2$, preferably no more than $1mm^2$.

19. A rotary valve according to claim 17, wherein the passage extends to a second port defined in the rotor that is positioned on the rotational axis and is in communication with the second port of the stator.

20. A rotary valve according to claim 19, wherein the liner has a base covering an end surface of the rotor that extends transversely to the rotational axis, the base having a passage that extends from the second port of the rotor to the second port of the stator so that the passage in the rotor is in communication with the second port of the stator through the passage in the liner.

21. A rotary valve according to claim 20, wherein the rotor has a boss formed on the end surface of the rotor protruding into a recess in the liner, the second port of the rotor being formed in the boss and the passage extending from the recess, the boss and the recess providing a seal therebetween.

22. A rotary valve according to claim 20, wherein the second port of the stator is defined in the annular surface of the stator.

23. A rotary valve according to claim 17, wherein the passage in the rotor communicates with a passage in the liner that is in communication with the second port of the stator.

24. A rotary valve according to claim 17, wherein the liner has a fixed position relative to the stator, and said at least one channel is a plurality of channels each in communication with one of the plurality of first ports of the stator and capable of communication with the first port of the rotor, depending on the rotational position of the rotor.

25. A rotary valve according to claim 17, wherein the rotor has an annular lip engaging the liner and retaining the rotor in the liner along the rotational axis.

26. A rotary valve according to claim 17, wherein the annular surface of the rotor is parallel to the rotational axis.

27. A rotary valve according to claim 17, wherein the annular surface of the stator is parallel to the rotational axis.

28. A rotary valve according to claim 17, wherein the stator is on a body that is arranged to allow attachment of a well plate comprising a plurality of wells corresponding to the plurality of first ports, the body defining channels connecting the wells to the corresponding first ports.

29. A rotary valve according to claim 1, wherein:
the plurality of first ports defined by the stator is arranged around the rotational axis facing the rotor;
the valve comprises a collection chamber extending in at least part of an annulus around the axis of rotation of the valve member,
the second port of the stator is in communication with the collection chamber, and
the rotor provides the passage, the passage extending between the collection chamber with which the passage is in communication and a position where the passage is capable of communication with any one of the plurality of first ports depending on the rotational position of the rotor.

30. A rotary valve according to claim 29, wherein the first ports, the passage, the collection chamber and the second port have cross-sectional areas of no more than 10mm$^2$, preferably no more than 1mm$^2$.

31. A rotary valve according to claim 29, wherein the rotor and the stator have interfacing contact surfaces that extend transversely to the rotational axis, the plurality of first ports and the second port opening in the contact surface of the stator.

32. A rotary valve according to claim 31, wherein the interfacing contact surfaces extend perpendicular to the rotational axis.

33. A rotary valve according to claim 31, wherein the valve further comprises a biasing arrangement arranged to bias the rotor against the stator.

34. A rotary valve according to claim 33, wherein the biasing arrangement comprises a resilient biasing element engaging the rotor.

35. A rotary valve according to claim 34, wherein the biasing arrangement further comprises a clamping ring attached to the stator, the resilient biasing element being arranged between the clamping ring and the rotor.

36. A rotary valve according to claim 25, wherein the passage is defined by a groove formed in the contact surface of the rotor.

37. A rotary valve according to claim 25, wherein the collection chamber is defined by a groove formed in the contact surface of one of the stator or the rotor.

38. A rotary valve according to claim 37, wherein the collection chamber is defined by a groove formed in the contact surface of the stator.

39. A rotary valve according to claim 29, wherein the rotor comprises a bearing stub and the stator comprises a bearing recess in which the bearing stub is mounted.

40. A rotary valve according to claim 29, wherein the stator is on a body that is arranged to allow attachment of a well plate comprising a plurality of wells corresponding to the plurality of first ports, the body defining channels connecting the wells to the corresponding first ports.

41. A rotary valve according to claim 40, wherein the body comprises first and second plates having interfacing contact surfaces, the first plate being arranged to allow attachment of the well plate, the contact surface of the base being formed in the second plate and each channel being formed by a through passage extending through the first plate to the contact surface of the first plate, a groove formed in the contact surface of one of the first plate and the second plate, and a through passage extending through the second plate from the contact surface of the second plate.

42. A rotary valve according to claim 41, wherein the first plate comprises a plurality of nozzles arranged to protrude into the wells of a well plate when attached to the first plate, the through passages that extend through the first plate extending through the nozzles.

43. A rotary valve according to claim 41, wherein the base further comprises a third plate, the second and third plates having interfacing contact surfaces, the base further comprising a channel formed by a through passage extending through the third plate to the contact surface of the third plate, and a groove formed in the contact surface of one of the second plate and the third plate.

44. An analysis apparatus for performing biochemical analysis of a sample using nanopores, the analysis apparatus comprising:
a sensor device that is capable of supporting plural nanopores and being operable to perform biochemical analysis of a sample using the nanopores;
at least one reservoir for holding material for performing the biochemical analysis;
a fluidics system configured to controllably supply material from the at least one reservoir to the sensor device; and
a plurality of containers for receiving respective samples, the fluidics system being configured to supply the samples selectively from the containers to the sensor device;
wherein the fluidics system includes a valve having an outlet port and a plurality of inlet ports corresponding to the plurality of containers and being configured to selectively connect one of the inlet ports to the output port, the fluidics system including channels connecting the containers to the corresponding inlet ports and channels connecting the outlet port to the sensor device; and
wherein the valve is a rotary valve according to claim 10.

* * * * *

UNITED STATES PATENT AND TRADEMARK OFFICE
CERTIFICATE OF CORRECTION

| | | |
|---|---|---|
| PATENT NO. | : 9,593,370 B2 | |
| APPLICATION NO. | : 13/876911 | |
| DATED | : March 14, 2017 | |
| INVENTOR(S) | : Anthony Jones | |

It is certified that error appears in the above-identified patent and that said Letters Patent is hereby corrected as shown below:

In the Claims

Claim 12, at Column 28, Line 17, replace "A rotary valve according to claim 7 wherein" with -- A rotary valve according to claim 7, wherein --

Claim 17, at Column 28, Line 40, replace "rotational axis inside a the liner" with -- rotational axis inside the liner --

Claim 44, at Column 30, Line 66, replace "wherein the valve is a rotary valve according to claim 10" with -- wherein the valve is a rotary valve according to claim 1 --

Signed and Sealed this
Thirtieth Day of May, 2017

Michelle K. Lee
*Director of the United States Patent and Trademark Office*